United States Patent
Smalling et al.

(10) Patent No.: US 11,478,216 B2
(45) Date of Patent: Oct. 25, 2022

(54) IMAGE PROCESSING APPARATUS, X-RAY DIAGNOSIS APPARATUS, AND ULTRASONIC DIAGNOSIS APPARATUS

(71) Applicants: Richard Smalling, Houston, TX (US); Canon Medical Systems Corporation, Otawara (JP)

(72) Inventors: Richard Smalling, Houston, TX (US); Andrew Kuhls-Gilcrist, Tustin, CA (US); Takuya Sakaguchi, Utsunomiya Tochigi (JP); Manabu Tanaka, Otawara Tochigi (JP)

(73) Assignees: Richard Smalling, Houston, TX (US); Canon Medical Systems Corporation, Otawara (JP)

( * ) Notice: Subject to any disclaimer, the term of this patent is extended or adjusted under 35 U.S.C. 154(b) by 893 days.

(21) Appl. No.: 16/177,043

(22) Filed: Oct. 31, 2018

(65) Prior Publication Data
US 2020/0129141 A1 Apr. 30, 2020

(51) Int. Cl.
A61B 8/08 (2006.01)
A61B 8/12 (2006.01)
A61B 6/00 (2006.01)
A61B 34/20 (2016.01)

(52) U.S. Cl.
CPC ............ *A61B 8/0883* (2013.01); *A61B 6/463* (2013.01); *A61B 6/5247* (2013.01); *A61B 8/12* (2013.01); *A61B 34/20* (2016.02)

(58) Field of Classification Search
None
See application file for complete search history.

(56) References Cited

U.S. PATENT DOCUMENTS

| | | | |
|---|---|---|---|
| 8,532,352 B2 | 9/2013 | Ionasec et al. | |
| 2012/0065498 A1* | 3/2012 | Redel | A61B 8/0883 600/424 |
| 2013/0261457 A1* | 10/2013 | Wei | A61B 8/4444 600/441 |
| 2014/0052241 A1 | 2/2014 | Harks et al. | |
| 2016/0354057 A1* | 12/2016 | Hansen | A61B 8/483 |

FOREIGN PATENT DOCUMENTS

JP 2014-524753 9/2014
JP 5670145 12/2014
JP 5670145 B2 * 2/2015

* cited by examiner

*Primary Examiner* — Amelie R Davis
*Assistant Examiner* — Marjan Saboktakin
(74) *Attorney, Agent, or Firm* — Oblon, McClelland, Maier & Neustadt, L.L.P.

(57) ABSTRACT

According to one embodiment, an image processing apparatus includes at least one of memory and processing circuitry. The memory stores a first medical image of a heart area acquired in a plurality of directions and a second medical image of the heart area acquired in real time. The processing circuitry is configured to set, based on the first medical image, each of a valve boundary line indicating a boundary between leaflets of a heart valve and an insertion point on an inner wall through which a catheter is inserted, generate a navigation graphic including the valve boundary line and the safety lines by generating a plurality of safety lines individually connecting the insertion point to ends of the valve boundary line, and superimpose the navigation graphic on the second medical image to generate a superimposed image.

19 Claims, 26 Drawing Sheets

| Image name | Control target | Selection | Flag | |
|---|---|---|---|---|
| Navigation graphic | Color | Stark white | 1 | ~31T |
| | | Pitch black | 0 | |
| | | Multiple colors | 0 | |
| | Line type | Solid line | 1 | |
| | | Dotted line | 0 | |
| | Display | On | 1 | |
| | | Off | 0 | |
| Volume image | Display | On | 0 | |
| | | Off | 1 | |

FIG. 9

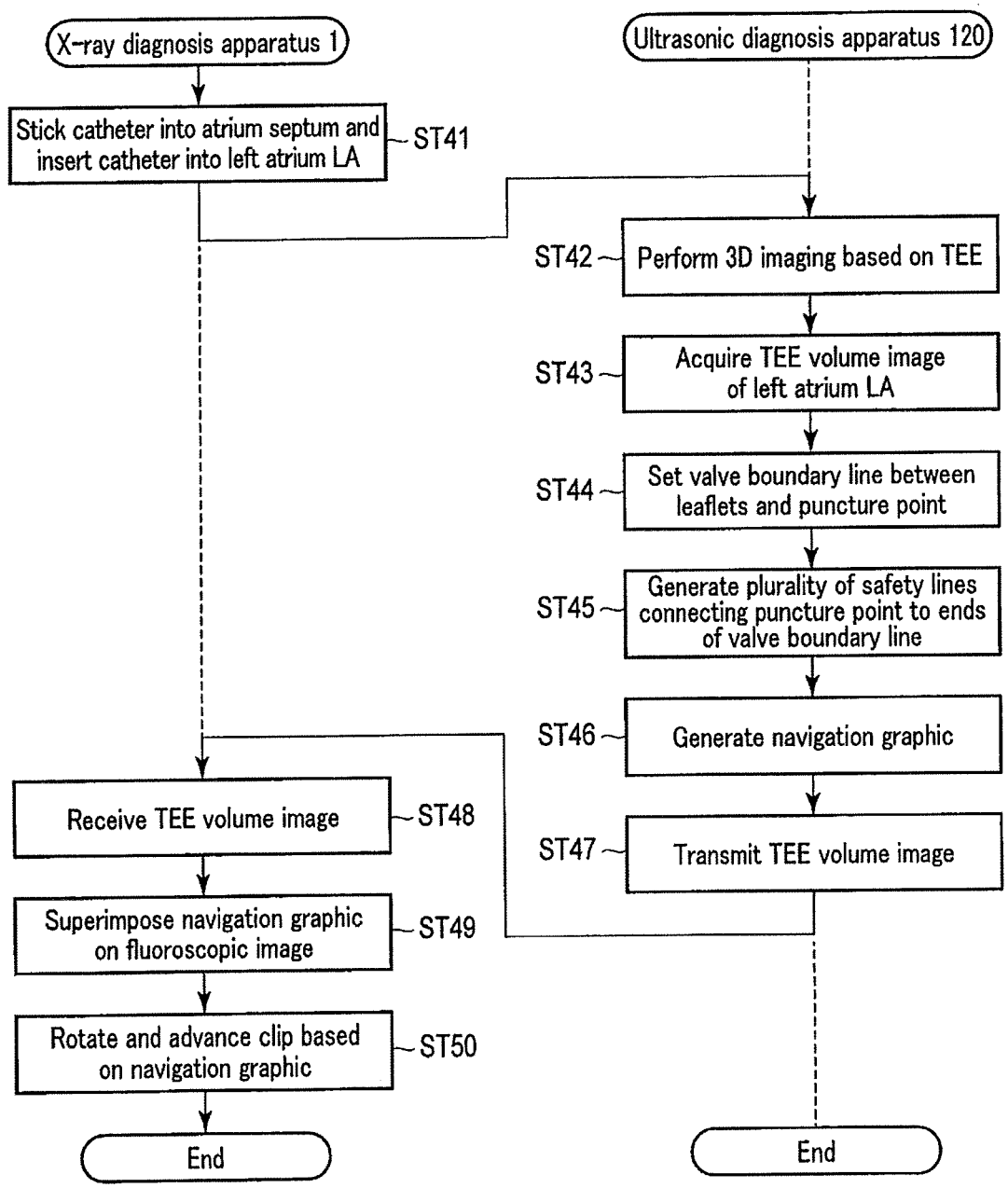
F I G. 17

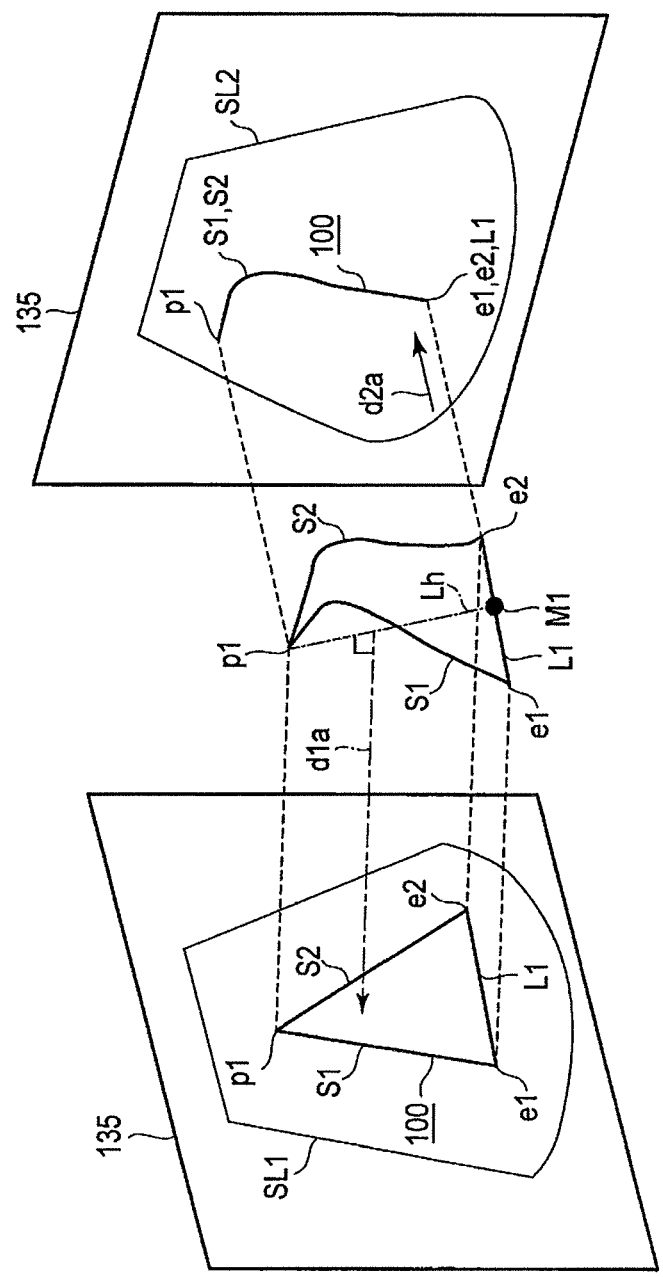
F I G. 22

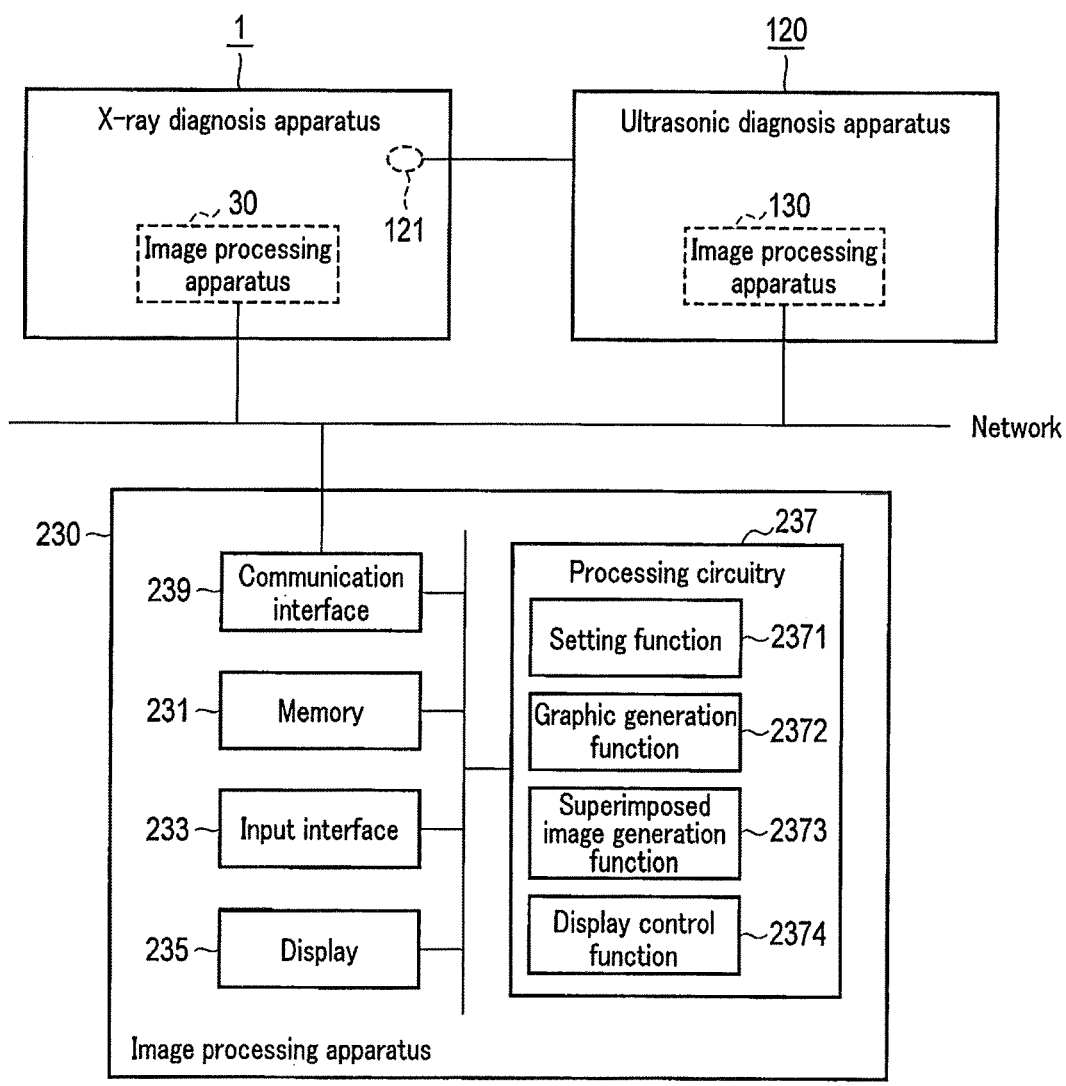
F I G. 23

IMAGE PROCESSING APPARATUS, X-RAY DIAGNOSIS APPARATUS, AND ULTRASONIC DIAGNOSIS APPARATUS

FIELD

Embodiments described herein relate generally to an image processing apparatus, an X-ray diagnosis apparatus, and an ultrasonic diagnosis apparatus.

BACKGROUND

In general, with respect to diagnosis or catheter treatment for disease in the heart valve, various medical image diagnosis apparatuses are known which generate images of the cardiac area. Examples of such a medical image diagnosis apparatus include an ultrasonic diagnosis apparatus and an X-ray diagnosis apparatus.

The ultrasonic diagnosis apparatus uses, for example, an ultrasonic Doppler method to display, in ultrasonic color images, a blood flow and motion of tissues near a valve orifice from which a back flow of blood spurts due to disease in the heart valve. When the back flow is viewed, a catheter treatment is performed to insert an indwelling device such as an artificial valve or a clip or a suturing device used to suture the valve.

The X-ray diagnosis apparatus displays, during such a catheter treatment, an X-ray image of the cardiac area into which the catheter has been inserted. However, the X-ray image does not display the cardiac wall or the heart valve.

Thus, the X-ray diagnosis apparatus preferably displays, on the X-ray image, a navigation graphic which allows a device at the tip of the catheter to be guided. The navigation graphic has a circular line illustrating the annulus and a straight line passing through the center of the annulus. In some cases, the X-ray image and the navigation graphic are displayed on an image processing apparatus instead of the X-ray diagnosis apparatus.

The navigation graphic as described above normally poses no problem, but the inventors' examinations indicate that the navigation graphic needs to be improved to allow enhancement of safety and accuracy of the catheter treatment. For example, the circular line and the straight line in the navigation graphic fail to indicate a safe range if the tip of the catheter is misaligned with the straight line, and thus, the catheter tip may collide against the inner wall of the cardiac chamber. Therefore, the navigation graphic needs to be improved to allow enhancement of safety of the catheter treatment. In addition, the circular line and the straight line in the navigation graphic fail to indicate the orientation of the heart valve, and thus, the rotation angle of the indwelling device may fail to coincide with the orientation of the heart valve. Therefore, the navigation graphic needs to be improved to allow enhancement of accuracy of the catheter treatment.

An object is to provide a navigation graphic which allows improvement of safety and accuracy of the catheter treatment.

BRIEF DESCRIPTION OF THE DRAWINGS

FIG. 9 is a schematic diagram depicting a setting table in a third modification of the first embodiment;

FIG. 17 is a flowchart illustrating operations in the fifth embodiment;

FIG. 22 is a schematic diagram illustrating a modification of the sixth embodiment;

FIG. 23 is a block diagram illustrating an image processing apparatus according to a seventh embodiment and peripheral components therefor;

DETAILED DESCRIPTION

According to one embodiment, an image processing apparatus includes at least one of memory and processing circuitry.

The memory is configured to store a first medical image of a heart area of a subject acquired in a plurality of directions and a second medical image of the heart area acquired in real time.

The processing circuitry is configured to set, based on the first medical image, each of a valve boundary line indicating a boundary between leaflets of a heart valve in a heart chamber and an insertion point on an inner wall of the heart chamber through which a catheter is inserted.

The processing circuitry is configured to generate a navigation graphic including the valve boundary line and the safety lines by generating a plurality of safety lines individually connecting the insertion point to ends of the valve boundary line at a distance from the inner wall.

The processing circuitry is configured to superimpose the navigation graphic on the second medical image to generate a superimposed image.

The processing circuitry is configured to display the superimposed image on a display.

Embodiments will be described below with reference to the drawings. In each embodiment, the mitral valve is used as an example of the heart valve. A puncture point is used as an example of an insertion point. As an example of a device held at a catheter tip, an indwelling device such as a clip (for example, MitraClip™) is used. However, the embodiments are not limited to these examples. As the heart valve, any valve such as the tricuspid valve, the aortic valve, and the pulmonary device can be used as needed. As the device held at the tip of the catheter, any treatment device such as a suturing device used to suture an artificial valve can be used as needed. The "insertion point" and the "puncture point" are interchangeable with an "insertion position" and a "puncture position". As the X-ray diagnosis apparatus, a biplane structure is described by way of example. However, the embodiments are not limited to this, and a single plane structure may be used.

An image processing apparatus provided in an X-ray diagnosis apparatus will mainly be described by way of example, but the embodiments are not limited to this. The description of the image processing apparatus provided in the X-ray diagnosis apparatus is similarly applicable to an image processing apparatus provided in an ultrasonic diagnosis apparatus and an image processing apparatus provided outside the diagnosis apparatus. Similarly, the description of the image processing apparatus provided in the ultrasonic diagnosis apparatus is similarly applicable to the image processing apparatus provided in the X-ray diagnosis apparatus and the image processing apparatus provided outside the diagnosis apparatus. This is because any image processing apparatus can execute image processing on each of a first medical image and a second medical image generated by each diagnosis apparatus.

First Embodiment

Figure 1:
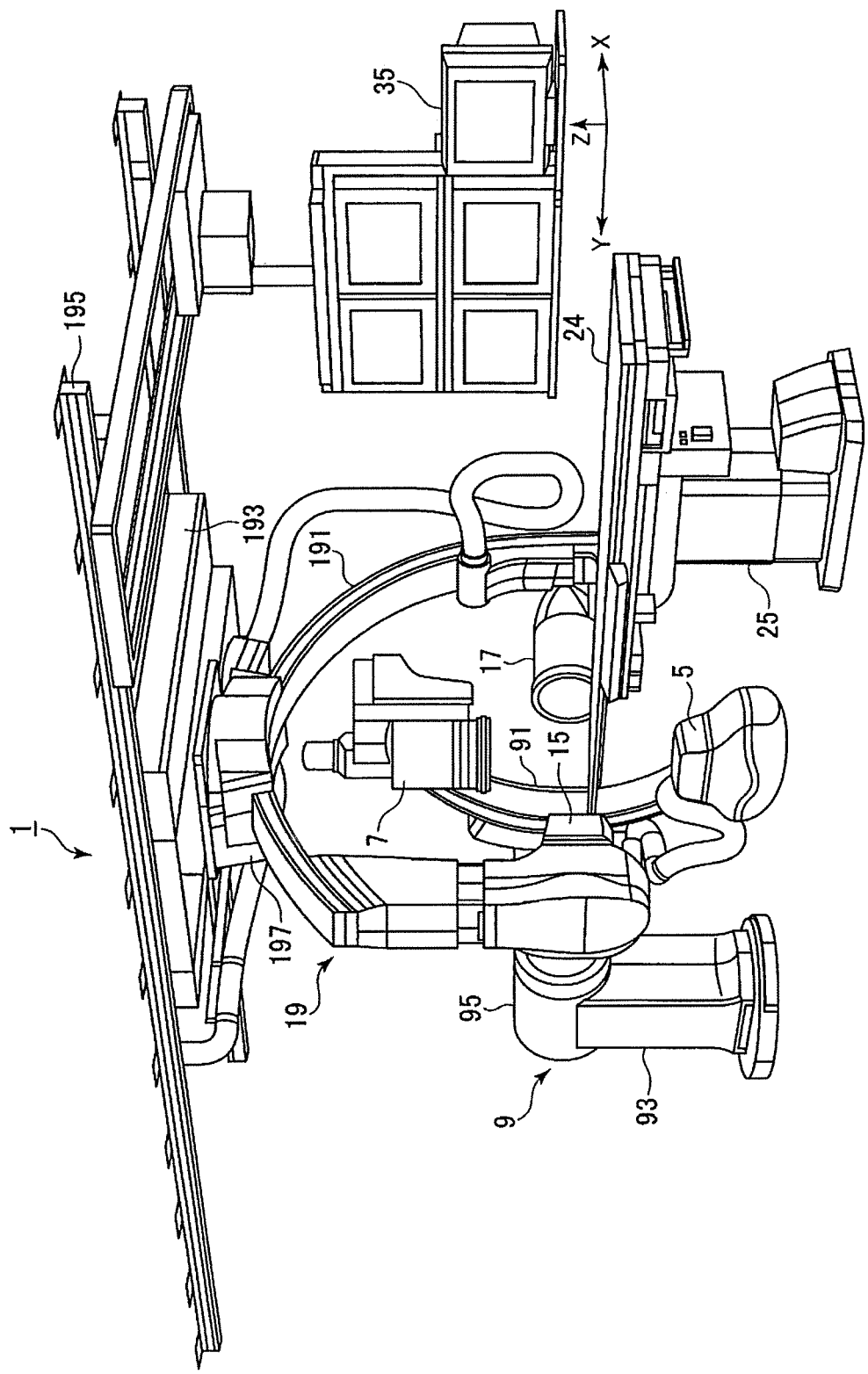
FIG. 1 is a schematic diagram depicting an appearance of an X-ray diagnosis apparatus according to a first embodiment.

FIG. 1 is a diagram depicting an appearance of an X-ray diagnosis apparatus according to the present embodiment. As depicted in FIG. 1, an X-ray diagnosis apparatus 1 according to the present embodiment comprises a plurality of support mechanisms (biplane structure).

Figure 2:
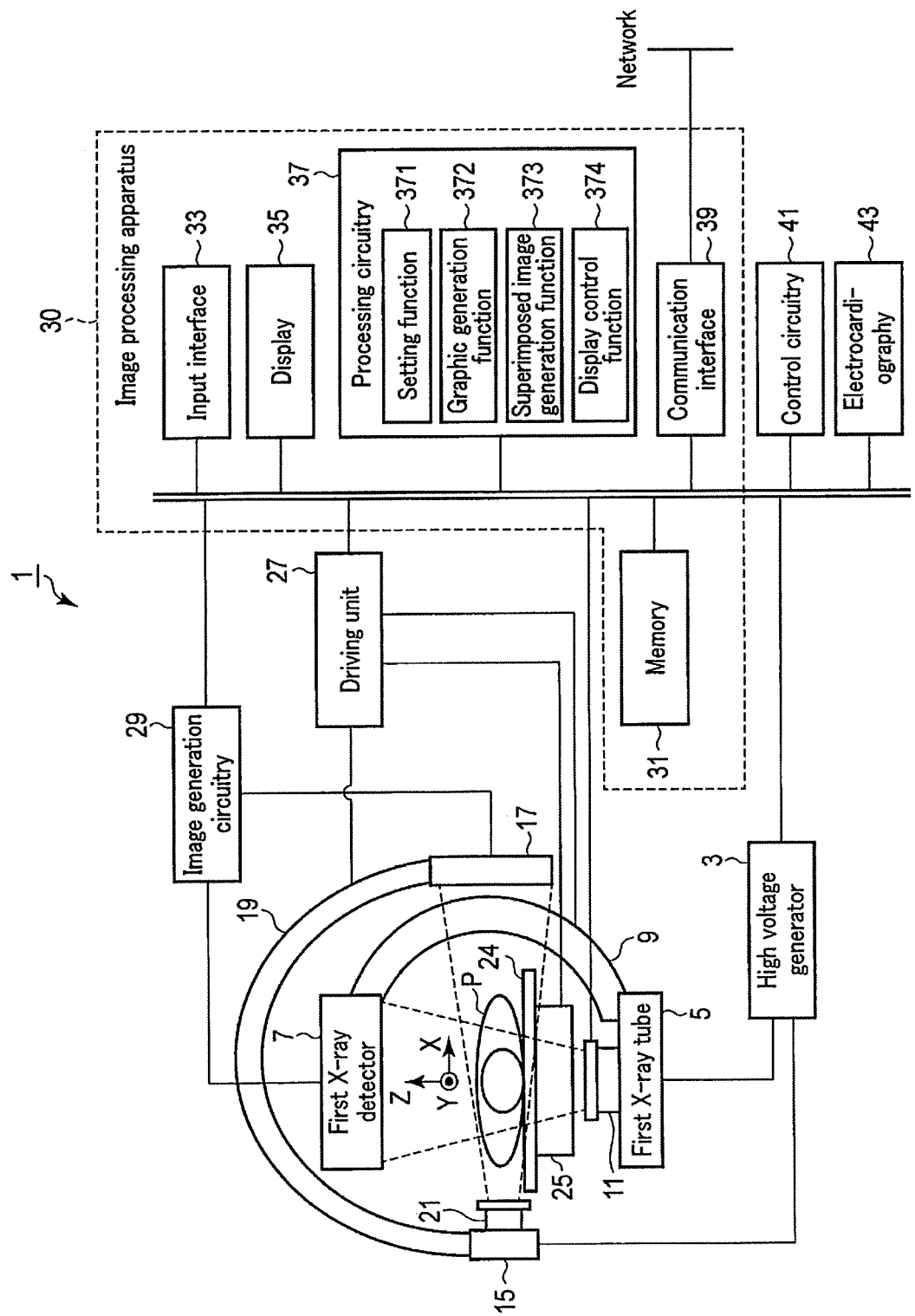
FIG. 2 is a block diagram depicting a configuration of the X-ray diagnosis apparatus according to the first embodiment.

FIG. 2 is a block diagram depicting a configuration of the X-ray diagnosis apparatus according to the first embodiment. The X-ray diagnosis apparatus 1 comprises a high voltage generator 3, a first X-ray tube 5, a first X-ray detector 7, a first support mechanism 9, a first collimator 11, a second X-ray tube 15, a second X-ray detector 17, a second support mechanism 19, a second collimator 21, a top plate 24, a bed 25, a driving unit 27, an image generation circuitry 29, an image processing apparatus 30, and control circuitry 41. The X-ray diagnosis apparatus 1 may connect to an electrocardiograph 43. The image processing apparatus 30 comprises at least one of memory 31, an input interface 33, a display 35, processing circuitry 37, and a communication interface 39. The image processing apparatus 30 need not necessarily be provided in the X-ray diagnosis apparatus 1 but may be provided as an external apparatus for the X-ray diagnosis apparatus.

The high voltage generator 3 generates a tube current which is supplied to the first X-ray tube 5 and the second X-ray tube 15 and a tube voltage which is applied to the first X-ray tube 5 and the second X-ray tube 15. The high voltage generator 3 is controlled by the control circuitry 41 to supply the tube current to the first X-ray tube 5 and the second X-ray tube 15 and to apply the tube voltage to the first X-ray tube 5 and the second X-ray tube 15.

Based on the tube current supplied by the high voltage generator 3 and the tube voltage applied by the high voltage generator 3, the first X-ray tube 5 generates an X-ray (hereinafter referred to as a first X-ray) at a focus of the X-ray (hereinafter referred to as a first focus). The first X-ray generated at the first focus is emitted to an object P via an X-ray emission window provided in a front surface of the first X-ray tube 5. A portion of the first X-ray generated at the first focus is shielded by the first collimator 11 provided between the first X-ray tube 5 and the X-ray emission window. That is, the first collimator 11 is moved in accordance with a first irradiation (emission) range received from the input interface 33 to limit the irradiation range of the first X-ray. The first X-ray tube 5 and the first collimator 11 are an example of an X-ray emitter recited in the claims.

The first X-ray detector 7 detects the first X-ray having passed through the object P after being generated by the first X-ray tube 5. For example, the first X-ray detector 7 comprises a flat panel detector (hereinafter referred to as a first FPD). The first FPD comprises a plurality of semiconductor detection elements. The semiconductor detection elements are classified into a direct conversion system and an indirect conversion system. The direct conversion system is a system which directly converts an incident X-ray into an electric signal. The indirect conversion system is a system which converts an incident X-ray into light using a phosphor and then converts the light into an electric system.

Electric signals generated by a plurality of semiconductor detection elements in conjunction with incidence of the first X-ray are output to an analog to digital converter (hereinafter referred to as an A/D converter) not depicted in the drawings. The A/D converter converts an electric signal into digital data. The A/D converter outputs digital data to the image generation circuitry 29. The first X-ray detector 7 may be an image intensifier. The first X-ray detector 7 is an X-ray detector recited in the claims.

The first support mechanism 9 movably supports the first X-ray tube 5 and the first X-ray detector 7. Specifically, the first support mechanism 9 comprises, for example, a C arm 91 and a C arm support unit 93. The C arm 91 is equipped with the first X-ray tube 5 and the first X-ray detector 7 such that the first X-ray tube 5 and the first X-ray detector 7 face each other. The C arm support unit 93 supports the C arm 91 such that the C arm 91 is slidable in a direction along the C shape of the C arm 91 (hereinafter referred to as a C direction).

The C arm support unit 93 supports the C arm 91 such that the C arm 91 is rotatable in a direction orthogonal to the C direction (hereinafter referred to as a C orthogonal direction) using, as a substantial center, a first connection unit 95 which connects the C arm 91 and the C arm support unit 93 together. The C arm support unit 93 can also support the C arm 91 such that the C arm 91 can be translated in a short axis direction (an X direction in FIG. 1, FIG. 2) and a long axis direction (a Y direction in FIG. 1, FIG. 2) of a top plate 24 described below. The C arm 91 supports the first X-ray tube 5 and the first X-ray detector 7 so as to enable a change in a distance between the first focus and the first X-ray detector 7 (a source image distance: hereinafter referred to as a first SID).

The second X-ray tube 15 generates an X-ray (hereinafter referred to as a second X-ray) at a focus of the X-ray (hereinafter referred to as a second focus) based on the tube current supplied by the high voltage generator 3 and the tube voltage applied by the high voltage generator 3. The second X-ray generated at the second focus is emitted to the object P via an X-ray emission window provided in a front surface of the second X-ray tube 15. A portion of the second X-ray generated at the second focus is shielded by the second collimator 21 provided between the second X-ray tube 15 and the X-ray emission window. That is, the second collimator 21 is moved in accordance with a second irradiation (emission) range received from the input interface 33 to limit the irradiation range of the second X-ray. The second X-ray tube 15 and the second collimator 21 are an example of the X-ray emitter recited in the claims.

The second X-ray detector 17 detects the second X-ray having passed through the object P after being generated by the second X-ray tube 15. For example, the second X-ray detector 17 comprises a second FPD. Electric signals generated by a plurality of semiconductor detection elements in conjunction with incidence of the second X-ray are output to the A/D converter not depicted in the drawings. The A/D converter converts an electric signal into digital data. The A/D converter outputs digital data to the image generation circuitry 29. The second X-ray detector 17 may be an image intensifier. The second X-ray detector 17 is the X-ray detector recited in the claims.

The second support mechanism 19 movably supports the second X-ray tube 15 and the second X-ray detector 17. Specifically, the second support mechanism 19 comprises, for example, an Ω arm 191 and an Ω arm support unit 193. The Ω arm 191 is equipped with the second X-ray tube 15 and the second X-ray detector 17 such that the second X-ray tube 15 and the second X-ray detector 17 face each other. The Ω arm support unit 193 supports the Ω arm 191 such that the Ω arm 191 is slidable in a direction along the Ω shape of the Ω arm 191 (hereinafter referred to as an Ω direction).

The Ω arm support unit 193 is installed so as to be movable along rails 195 provided on a ceiling. The rails 195 are provided on the ceiling, for example, parallel to the long axis direction of the top plate 24. The Ω arm support unit 193 supports the Ω arm 191 such that the Ω arm 191 is rotatable in a direction orthogonal to the Ω direction (hereinafter referred to as Ω orthogonal direction) using, as a substantial center, a second connection unit 197 which connects the Ω arm 191 and the Ω arm support unit 193 together. The Ω arm support unit 193 can also support the Ω arm 191 such that the Ω arm 191 can be translated in the short axis direction (the X direction in FIG. 1, FIG. 2) and the long axis direction (the Y direction in FIG. 1, FIG. 2) of the top plate 24 described below. The Ω arm 91 supports the second X-ray tube 15 and the second X-ray detector 17 so as to enable a change in a distance between the second focus and the second X-ray detector 17 (a source image distance: hereinafter referred to as a second SID).

The bed 25 comprises the top plate 24 on which the object P is laid. The object P is laid on the top plate 24.

The driving unit 27 is controlled by the control circuitry 41 to drive the first support mechanism 9, the second support mechanism 19, and the bed 25. Specifically, the driving unit 27 supplies a driving signal corresponding to a control signal from the control circuitry 41 to the C arm support unit 93, to slide the C arm 91 in the C direction and rotate the C arm 91 in the C orthogonal direction. The driving unit 27 supplies a driving signal corresponding to a control signal from the control circuitry 41 to the Ω arm support unit 193, to slide the Ω arm 191 in the Ω direction and rotate the Ω arm 191 in the Ω orthogonal direction.

During X-ray imaging, the object P laid on the top plate 24 is arranged between the first X-ray tube 5 and the first X-ray detector 7 and between the second X-ray tube 15 and the second X-ray detector 17. The driving unit 27 outputs the position of the first X-ray tube 5 with respect to the top plate 24 (or the position of the first support mechanism 9) and the position of the second X-ray tube 15 with respect to the top plate 24 (or the position of the second support mechanism 19) to the control circuitry 41 and the like.

The driving unit 27 is controlled by the control circuitry 41 to drive and move the top plate 24. Specifically, the driving unit 27 slides the top plate 24 in the short axis direction (the X direction in FIG. 1, FIG. 2) the top plate 24 or the long axis direction (the Y direction in FIG. 1, FIG. 2) of the top plate 24 based on a control signal from the control circuitry 41. The driving unit 27 elevates and lowers the top plate 24 in the vertical direction (a Z direction in FIG. 1, FIG. 2). The driving unit 27 may rotate the top plate 24 in order to tilt the top plate 24, using at least one of the long axis direction and the short axis direction as a rotation axis (an X axis, a Y axis in FIG. 1).

The driving unit 27 outputs the position of the first support mechanism 9 (hereinafter referred to as a first position) and the position of the second support mechanism 19 (hereinafter referred to as a second position) to the control circuitry 41. The first position and the second position may be output from the first support mechanism 9 and the second support mechanism 19, respectively, to the control circuitry 41.

The driving unit 27 outputs a relative positional relation between the first X-ray tube 5 and the top plate 24 (hereinafter referred to as a first relative position) to the control circuitry 41. The driving unit 27 outputs a relative positional relation between the second X-ray tube 15 and the top plate 24 (hereinafter referred to as a second relative position) to the control circuitry 41.

The first relative position is, for example, the angle of the C arm 91 with respect to the top plate 24 (inclination) and the angle of sliding of the C arm 91 (hereinafter referred to as the arm angle). The inclination and the arm angle are, for example, Euler angles based on an isocenter with respect to the object P. The driving unit 27 may drive the first X-ray detector 7 in order to optionally rotate the first X-ray detector 7 in accordance with the position of the first support mechanism 9, the angle of the C arm 91, and the like.

The second relative position is, for example, the angle of the Ω arm 191 with respect to the top plate 24 (inclination) and the arm angle of sliding of the Ω arm 191. The inclination and the arm angle are, for example, Euler angles based on the isocenter with respect to the object P. The driving unit 27 may drive the second X-ray detector 17 in order to optionally rotate the second X-ray detector 17 in accordance with the position of the second support mechanism 19, the angle of the Ω arm 191, and the like.

Based on an output from the first X-ray detector 7, the image generation circuitry 29 generates an X-ray image of the cardiac area of the object P in real time based on an output from the first X-ray detector 7. Based on an output from the second X-ray detector 17, the image generation circuitry 29 generates an X-ray image of the cardiac area of the object P in real time based on an output from the second X-ray detector 7. For example, the image generation circuitry 29 executes preprocessing on digital data output from the first X-ray detector 7 and the second X-ray detector 17. The preprocessing is correction for variation in the sensitivity of each of the first X-ray detector 7 and the second X-ray detector 17 among channels and correction for a significant decrease in signal level or data missing caused by an X-ray absorber such as metal.

The image generation circuitry 29 generates two X-ray images corresponding to the first relative position and the second relative position, respectively, based on the preprocessed digital data. The image generation circuitry 29 outputs the generated X-ray images to the memory 31 and the display 35.

The memory 31 comprises a memory in which electric information is recorded, that is, any of a ROM (Read Only Memory), a RAM (Random Access Memory), HDD (Hard Disk Drive), and an image memory, and a peripheral circuitry accompanying the memory, such as a memory controller or a memory interface. The memory 31 stores first medical images of the cardiac area of the object P pre-imaged in a plurality of directions, and a second medical image which is an X-ray image generated by the image generation circuitry 29. The second medical image is a live image of the cardiac area of the object obtained in real time. "In real time" means sequential displaying or processing of an image in parallel with sequential acquisition of the image. The meaning of "in real time" is the same in each embodiment described hereinafter.

The first medical image may be an X-ray volume image or a plurality of two-dimensional X-ray contrast images, and the second medical image may be a fluoroscopic image. The X-ray volume image may be a three-dimensional image acquired by the X-ray diagnosis apparatus or a three dimensional CT image acquired by an X-ray computed tomography (CT) apparatus. The first medical image may be an ultrasonic volume image, and the second medical image may be a fluoroscopic image.

The memory stores a superimposed image generated by the processing circuitry 37, a control program for the X-ray diagnosis apparatus 1, a program for the image processing apparatus 30, a diagnosis protocol, an operator's command sent from the input interface 33, a group of various data such as imaging conditions and fluoroscopy conditions for X-ray imaging, various data sent via the input interface 33 and a network, a first X-ray dose, a second X-ray dose, and the like. The memory may store the first relative position, the second relative position, the first irradiation range, and the second irradiation range.

The memory 31 stores first X-ray irradiation conditions for generation of first X-ray and second X-ray irradiation (emission) conditions for generation of a second X-ray. The X-ray irradiation conditions include conditions for radiation quality of the X-ray (the tube voltage, the tube current, and the like), an irradiation time, an irradiation interval, apertures of X-ray diaphragms 11, 21, the product of the tube current (mA) and the irradiation time (s) (hereinafter referred to as a tube current-time lapse product (mAs)), the thickness (or the type) of a radiation quality adjustment filter selected via the input interface 33, a field of view (FOV), and an irradiation rate (the number of X-ray irradiations per second).

The memory stores first geometric conditions for each irradiation (generation) of the first X-ray and second geometric conditions for every irradiation (generation) of the second X-ray. The geometric conditions include the position of the top plate 24, the position of the C arm 91, the angle of the C arm 91, an irradiation direction of each X-ray (first direction, second direction), each SID, and each FPD rotation angle.

The input interface 33 is an interface related to, for example, a network or an external storage device not depicted in the drawings. Data such as X-ray images and analysis results obtained by the X-ray diagnosis apparatus 1 can be transferred to another apparatus via the input interface 33 and the network.

The input interface 33 allows inputting of the X-ray irradiation conditions, imaging positions for the first X-ray tube and the second X-ray tube, the irradiation ranges, the first direction, the second direction, and the like. Specifically, the input interface 33 loads various commands, orders, information, selections, and settings from the operator into the X-ray diagnosis apparatus 1. The imaging position is defined by, for example, an angle to the isocenter. For example, when the imaging position is assumed to be a start point in each of a first oblique direction (RAO), a second oblique direction (LAO), a caudo-cranial direction (CRA), a cranio-caudal direction (CAU) and the isocenter is assumed to be the origin of three orthogonal axes, the angle of a fluoroscopic position at the start point is 0°.

The input interface 33 is realized by, for example, a trackball, switch buttons, a mouse, a keyboard, a touchpad which executes an input operation by a touch on an operation screen, and a touch panel display in which a display screen and a touchpad are integrated. The input interface 33 is connected to the control circuitry 41 and the processing circuitry 37, converts an input operation, which was received from the operator, to an electric signal, and outputs the electric signal to the control circuitry 41 and the processing circuitry 37. In the meantime, in this specification, the input interface 33 is not limited to circuitry including physical operation components such as a mouse and a keyboard. Examples of the input interface 33 include electric signal processing circuitry which receives an electric signal corresponding to an input operation from an external input device provided separately from the apparatus, and outputs this electric signal to the control circuitry 41 and the processing circuitry 37.

The display 35 is controlled by the control circuitry 41 and the processing circuitry 37 to display the medical images, the navigation graphic, the superimposed image, and the like. The display 35 comprises internal circuitry which supplies signals for display to a display main body and peripheral circuitry comprising a connector and a cable to connect the display to the internal circuitry.

The processing circuitry 37 comprises a processor and a memory not depicted in the drawings, and the above-described various types of information input or set via the input interface 33 are saved to the memory. The processor integrally controls units of the image processing apparatus 30 based on the input information and the setting information, and allows the display 35 to display the second medical image with the navigation graphic superimposed thereon.

Specifically, the processor of the processing circuitry 37 invokes and executes a program in the memory 31 to implement a setting function 371, a graphic generation function 372, a superimposed image generation function 373, or a display control function 374 corresponding to the program. As described above with reference to FIG. 2, the single processing circuitry 37 implements the setting function 371, the graphic generation function 372, the superimposed image generation function 373, and the display control function 374. However, the present embodiment is not limited to this. A plurality of independent processors may be combined together to form processing circuitry so that each of the processors executes the corresponding program to implement the corresponding function. The assignment of the setting function 371, the graphic generation function 372, the superimposed image generation function 373, or the display control function 374 is for convenience and can be changed as needed. For example, a setting process of the setting function 371 may be executed by the graphic generation function 372.

Figure 3:
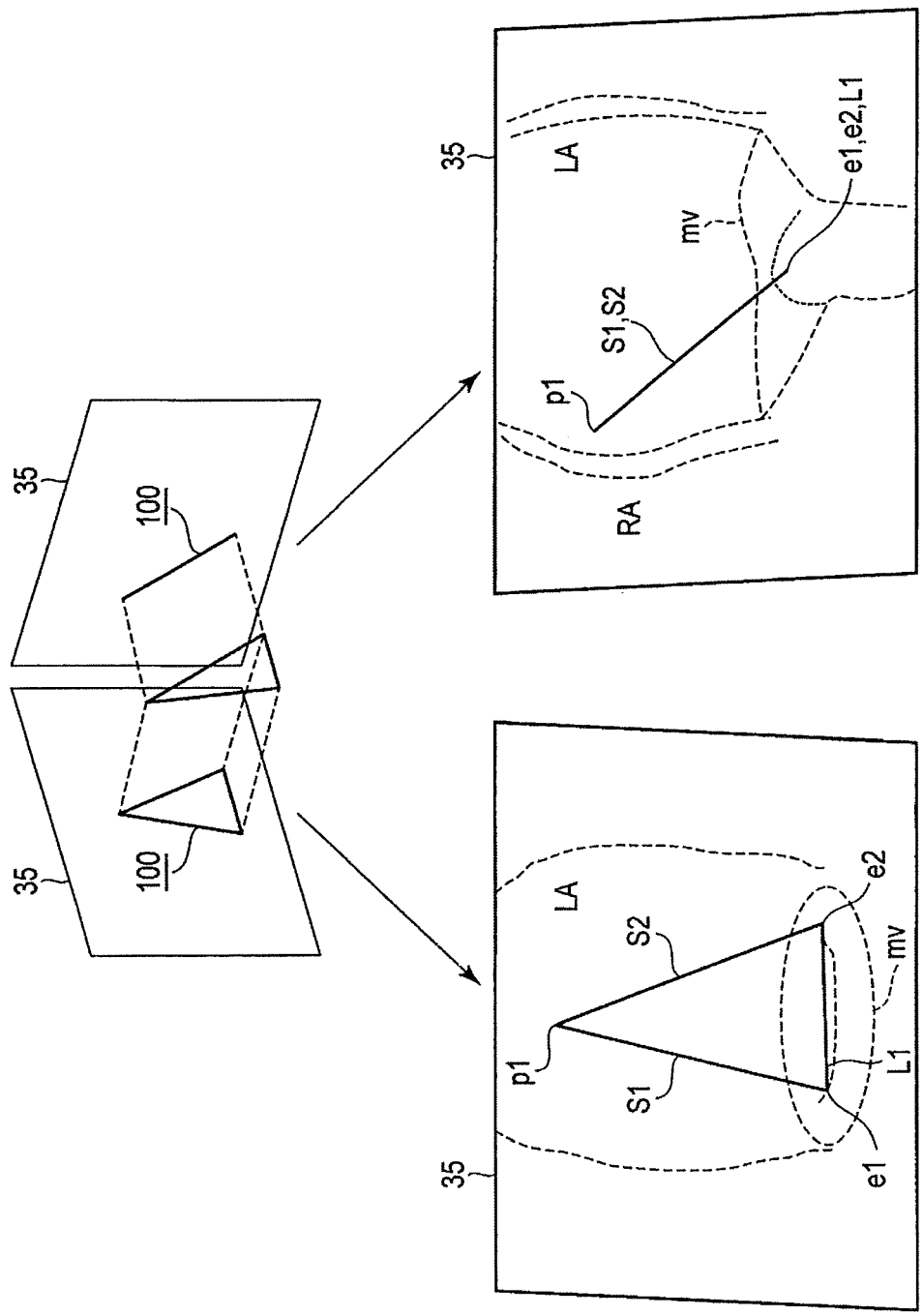
FIG. 3 is a schematic diagram illustrating a setting function in the first embodiment.

The setting function 371 sets a valve boundary line indicating boundaries between leaflets of the heart valve in the cardiac chamber and an insertion point on the inner wall of the cardiac chamber through which a catheter is inserted. For example, as depicted in FIG. 3, a puncture point p1 as an insertion point and a plurality of ends e1, e2 at boundaries between the leaflets of a mitral valve my in a left atrium LA are assumed to be designated in accordance with operation of the input interface 33. The setting function sets the designated puncture point p1, and sets a boundary line L1 which is a straight line connecting the designated plurality of ends e1, e2 together. For example, when a plurality of points on the boundaries between the leaflets are designated, the setting function 371 may set a valve boundary line which is a broken like or a curve connecting the plurality of points together. In FIG. 3, the right atrium is denoted by RA.

The graphic generation function 372 generates a plurality of safety lines S1, S2 individually connecting the puncture point p1 to the ends e1, e2 of the valve boundary line at a distance from the inner wall to generate a navigation graphic 100 comprising the valve boundary line L1 and the safety lines S1, S2. For example, when the puncture point p1 is designated in accordance with an operation of the input interface 33 by the operator, the graphic generation function 372 generates a plurality of safety lines which are straight lines or curves connecting the puncture point to the plurality of ends of the valve boundary line. For example, when the puncture point and the curvature are designated, the graphic generation function 372 generates a plurality of safety lines which are curves having the curvature and connecting the puncture point to the plurality of ends of the valve boundary line. The "safety lines" may also be referred to as "guide scope lines". The navigation graphic 100 means each of a three-dimensional graphic on a three-dimensional space (a graphic defined by three-dimensional coordinates) and a two-dimensional graphic (a graphic defined by two-dimensional coordinates) corresponding to the three-dimensional graphic projected on a two-dimensional space. In the present embodiment, the navigation graphic is a three-dimensional graphic immediately after the safety lines are generated. The navigation graphic as a three-dimensional graphic is turned into a two-dimensional graphic by being projected on the two-dimensional space.

The superimposed image generation function 373 generates a superimposed image by superimposing the navigation graphic on the second medical image. The "navigation graphic" may also be referred to as a "guide graphic" or a "guide line".

The display control function 374 allows the display 35 to display the superimposed image.

The communication interface 39 is a circuit which communicates with an external apparatus by wire, by radio, or by both. The external apparatus is, for example, a modality, the image processing apparatus, a server included in any of a radiological information system (RIS), a hospital information system, (HIS), and a picture archiving and communication system (PACS), or any other workstation.

The control circuitry 41 comprises a central processing unit (CPU) and a memory not depicted in the drawings. The control circuitry 41 temporarily stores, in the memory not depicted in the drawings, information sent via the input interface 33, such as the operator's command, the imaging position, the imaging direction of the first X-ray tube 5 (first direction), the imaging direction of the second X-ray tube 15 (second direction), the first irradiation range, the second irradiation range, the first X-ray conditions, and the second X-ray conditions. The control circuitry 41 controls the high voltage generator 3, the first X-ray detector 7, the second X-ray detector 17, the first collimator 11, the second collimator 21, the driving unit 27, and the image generation circuitry 29 in accordance with the operator's command, the imaging position, the first direction, the second direction, the first irradiation range, the second irradiation range, the first X-ray conditions, the second X-ray conditions, and the like stored in the memory.

The electrocardiograph (ECG) 43 records a temporal variation in electrical phenomenon in the heart of the object P in a graph, that is, obtains an electrocardiogram (ECG waveform). An electrocardiographic wave detected by the electrocardiograph 43 is stored in the internal memory and sent to the processing circuitry 37 as needed. The electrocardiographic wave is then used to display the navigation graphic in synchronism with an electrocardiographic waveform.

Figure 4:
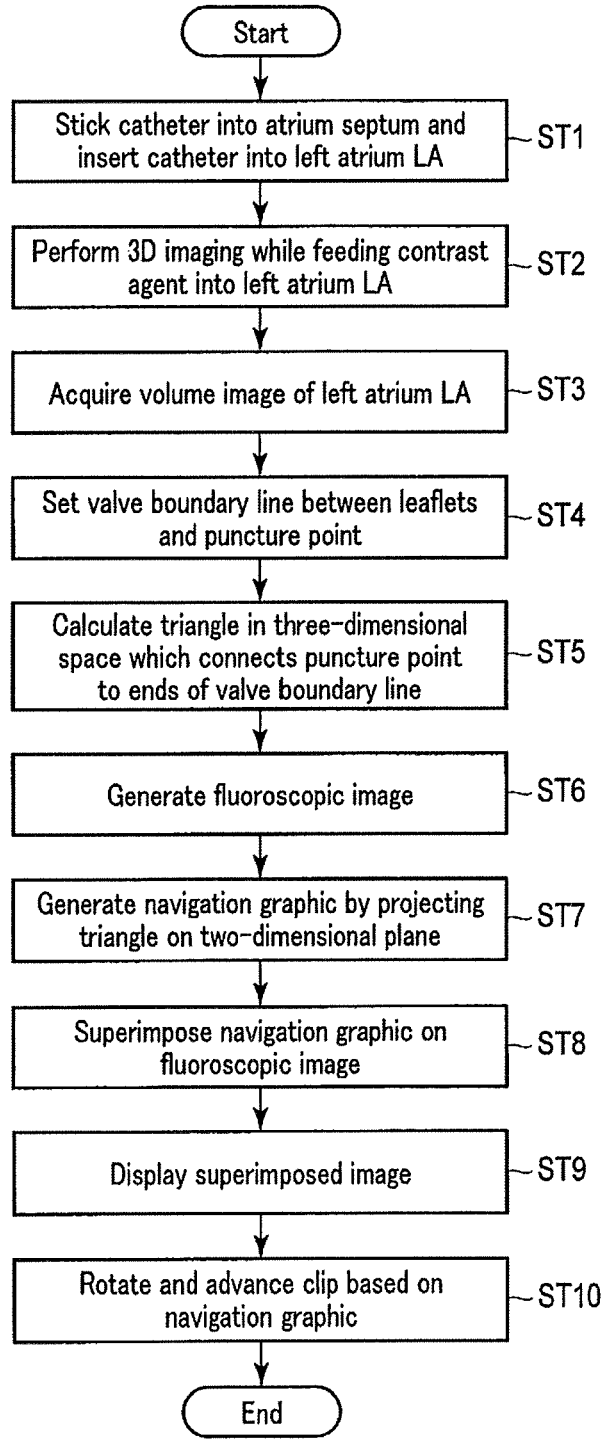
FIG. 4 is a flowchart illustrating operations in the first embodiment.

Now, operations of the X-ray diagnosis apparatus configured as described above will be described using a flowchart in FIG. 4 and a schematic diagram in FIG. 5. The following operations will be described mainly in conjunction with a process of generating the navigation graphic during a catheter treatment in which a clip is deployed to deal with mitral incompetence. A back flow through the mitral valve of the object (mitral incompetence) is assumed to have been confirmed in a preparation stage by the ultrasonic Doppler method.

In step ST1, while referencing a fluoroscopic image, the operator moves the catheter from the femoral vein of the object P to the right atrium RA, sticks (punctures) the catheter into the atrial septum, and inserts the catheter into the left atrium LA.

In step ST2 and step ST3, the operator inserts a pigtail catheter into the left atrium LA and performs 3D imaging while feeding a contrast agent into the left atrium LA. For example, with the C arm 91 rotated around the body axis of the object P, the first X-ray detector 7 detects the first X-ray radiated from the first X-ray tube 5 to the cardiac area of the object P. The image generation circuitry 29 generates a volume image of the left atrium LA based on an output from the first X-ray detector 7 and saves the volume image to the memory 31. Consequently, the X-ray diagnosis apparatus 1 acquires the volume image of the left atrium LA. The volume image corresponds to the first medical image used to generate the navigation graphic.

In step ST4, the processing circuitry 37 of the image processing apparatus 30 allows the display 35 to display the volume image saved in the memory 31. For example, as depicted in FIG. 3, the setting function 371 of the processing circuitry 37 sets the valve boundary line L1 between the leaflets of the mitral valve mV in the left atrium LA and the puncture point p1 for the catheter in accordance with an operation of the input interface 33 by the operator. To set the valve boundary line L1, a sulcus located midway between the mitral leaflets may be designated or both ends of the sulcus located midway between the mitral leaflets may be designated.

In step ST5, the graphic generation function 372 of the processing circuitry 37 calculates a triangle in the three-dimensional space which is formed by connecting the puncture point p1 to the ends e1, e2 of the valve boundary line L1 with the safety lines S1, S2. As depicted in the right of FIG. 3, a line corresponding to overlapping safety lines S1, S2 is defined as a trajectory of a catheter tip. As depicted in the left of FIG. 3, the range between the safety lines S1, S2 indicates a safe range within which the moving catheter tip is inhibited from colliding against the inner wall.

In step ST6, with the C arm 91 and the Ω arm 191 remaining stationary, the X-ray diagnosis apparatus 1 performs X-ray imaging. That is, the X-ray diagnosis apparatus 1 radiates the first X-ray and the second X-ray to the cardiac area of the object P in the orthogonal directions to generate fluoroscopic images based on outputs from the first X-ray detector 7 and the second X-ray detector 17. The first X-ray and the second X-ray may be radiated at the same time, or either one of the X-rays may be radiated. When either one of the X-rays is radiated, the radiated X-ray may be switched in accordance with the operation of the input interface 33 by the operator. In either case, the generated fluoroscopic images are saved to the memory 31.

In step ST7, the graphic generation function 372 generates the navigation graphic 100 by projecting the triangle in the three-dimensional space calculated in step ST5 on a two-dimensional plane.

In step ST8, the superimposed image generation function 373 of the processing circuitry 37 generates a superimposed image in which the navigation graphic 100 is superimposed on the fluoroscopic image.

In step ST9, the display control function 374 of the processing circuitry 37 allows the display 35 to display the superimposed image. The fluoroscopic image in the superimposed image is a real-time image, and the navigation graphic 100 basically remains still.

Figure 5:
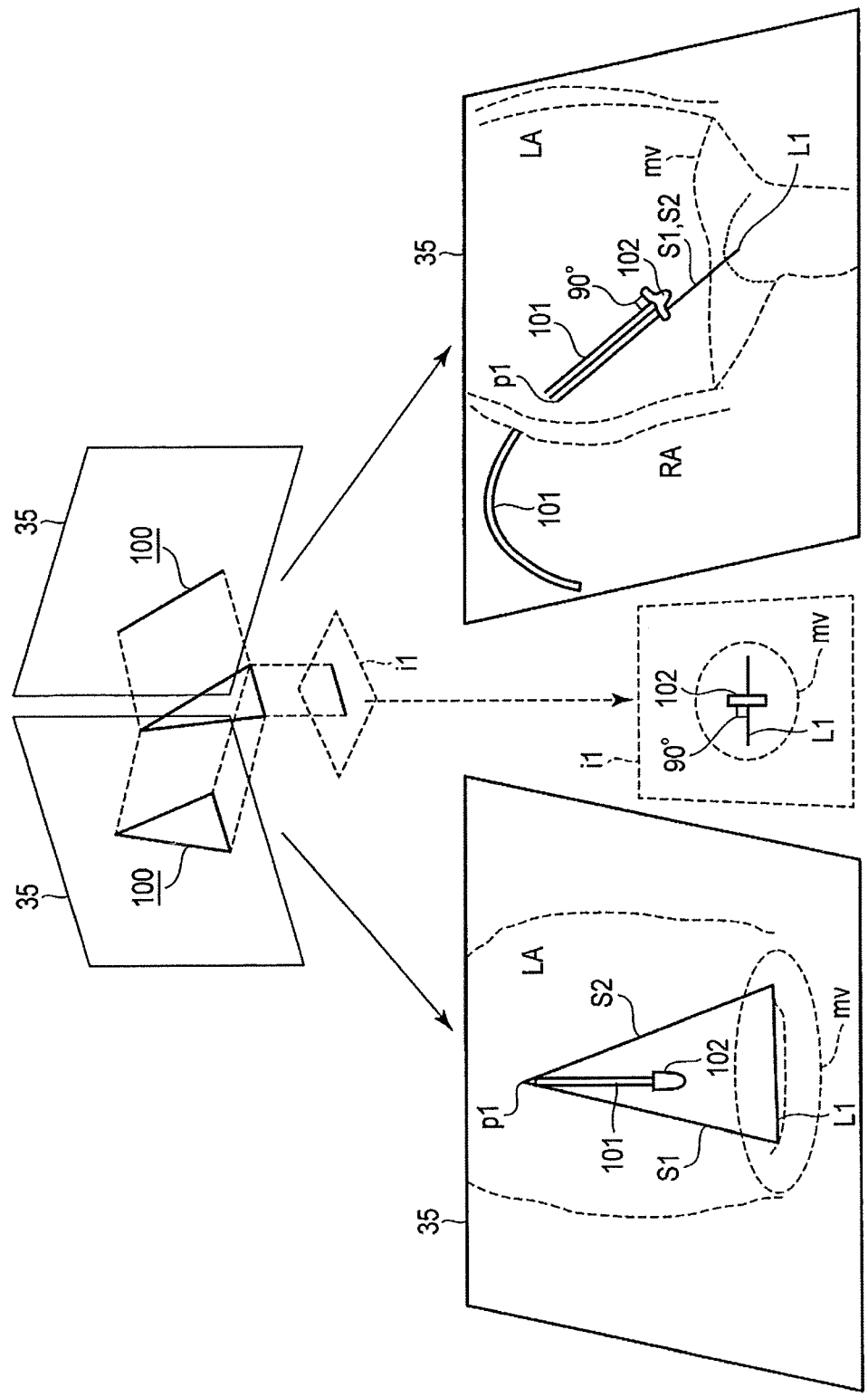
FIG. 5 is a schematic diagram illustrating operations in the first embodiment.

In step ST10, as depicted in FIG. 5, the operator advances a clip 102 installed at the tip of a catheter 101 while referencing the navigation graphic 100 for two directions displayed on the display 35. Consequently, the clip 102 can be smoothly guided to a position between the leaflets of the mitral valve mv. When the clip 102 approaches the mitral valve mv, the operator operates the catheter 101 to rotate the clip 102 around the axis of the tip of the catheter 101. The operator adjusts a longitudinal direction of the catheter with the clip 102 open such that the longitudinal direction crosses the valve boundary line L1 at right angles as depicted in a plan view i1. This adjustment is intended to rotate the clip 102 in a direction in which the leaflets, which are opened or closed at the valve boundary line L1, are narrowed. However, the plan view i1 is depicted to facilitate understanding and is not displayed on the display 35.

The operator advances the clip 102 from the left atrium LA to a left ventricle LV and uses the clip 102 to clip the leaflets of the mitral valve my. The clip 102 is shaped like an arrow, for example, similarly to MitraClip™, and configured such that the arrow is closed using the tip as a support to clip the leaflets. After clipping the leaflets using the clip 102, the operator deploys the clip 102 in the mitral valve my and removes the catheter 101.

Subsequently, when stoppage of a back flow through the mitral valve my of the object P (remedy of the mitral incompetence) is confirmed based on the ultrasonic Doppler method, the catheter treatment is completed.

In the above description, the biplane structure is used in step ST10. However, the present embodiment is not limited to this. For example, a single plane structure may be used to move the position of the C arm according to the imaging direction so as to allow alternate referencing of the navigation graphic 100 for the first direction and the navigation graphic 100 for the second direction.

As described above, based on the first medical image, the following are set: the valve boundary line indicating the boundaries between the leaflets of the heart valve in the cardiac chamber and the insertion point on the inner wall of the cardiac chamber through which the catheter is inserted, according to the first embodiment. A plurality of safety lines are generated which individually connect the puncture point to the ends of the valve boundary line at a distance from the inner wall, and thus, a navigation graphic comprising the valve boundary line and the safety lines is generated. The navigation graphic is superimposed on the second medical image to generate a superimposed image. The superimposed image is displayed on the display. Therefore, the first embodiment allows provision of a navigation graphic which enables improvement of safety and accuracy of a catheter treatment.

As a result of the catheter treatment using the navigation graphic 100, a risk of a failure in procedure is reduced, enabling enhancement of the operator's confidence and a reduction in total procedure time.

The navigation graphic is a graphic in which three points connecting two of the plurality of safety lines and the valve boundary line together form angles. Such a navigation graphic is not limited to the above-described triangle, but any graphic having three sides at least one of which is a curve and three angles may be used. For example, any graphic may be used in which the valve boundary line is a straight line and in which two sides corresponding to the plurality of safety lines are curves, the graphic having three angles. The navigation graphic may form a flat surface or a curved surface enclosed by the plurality of safety lines and the valve boundary line.

The plurality of safety lines may substantially overlap one another to indicate a trajectory of the catheter when the second medical image is acquired in the first direction in which the projection area of the surface formed by the navigation graphic is minimized. Alternatively, each of the plurality of safety lines may indicate the limit of the trajectory of the catheter when the second medical image is acquired in the second direction in which the projection area of the surface formed by the navigation graphic is maximized. When the projection area of the surface formed by the navigation graphic is maximized, the shape of the surface formed by the navigation graphic is not limited to the triangle, and any shape may be used so long as the navigation graphic is inhibited from coming into contact with the inner wall. However, the triangle is taken herein as an example.

For example, in conjunction with the indicated limit of the trajectory, the operator advances the clip 102 through the center of the triangle serving as the navigation graphic 100 in the second direction. The present embodiment is not limited to the center of the triangle, and the clip 102 may be advanced according to a back-flow position if the back-flow position is on the right side or left side of the valve boundary line L1. In conjunction with the indicated trajectory, the rotation angle may be set such that the clip 102 may overlap the safety lines S1, S2 in the first direction, with the open clip 102 viewed exactly laterally. This allows the clip 102 to be reliably guided.

In addition, for example, for the clip 102, not only a traveling direction of the catheter 101 but also the rotation angle of the clip 102 needs to be adjusted. The clip 102 fails to clip the leaflets of the mitral valve my unless the clip 102 is rotated into the correct direction. Thus, in the present embodiment, the navigation graphic 100 is a graphic having the valve boundary line L1 instead of a circle and lines so as to allow the rotation angle of the clip 102 to be identified. The operator advances the clip 102 while rotationally operating the C arm 91 (or using the biplane) to observe the superimposed image for a plurality of directions.

Thus, compared to the conventional navigation graphic, the navigation graphic 100 of the present embodiment allows improvement of safety and accuracy of the catheter treatment.

Techniques related to the conventional navigation graphic include [1] a planning line for chronic total occlusion (CTO) and [2] needle guidance software.

The [1] planning line for CTO is a single curve, and thus, needs to be improved to allow enhancement of the safety and accuracy similarly to the conventional navigation graphic.

The [2] needle guidance software plans the direction in which and the distance over which the needle is stuck based on 3D image data pre-acquired. However, the needle guidance involves a single straight line and thus, needs to be improved to allow enhancement of the safety and accuracy similarly to the conventional navigation graphic.

That is, compared to the related techniques [1], [2], the navigation graphic 100 of the present embodiment has been improved to allow enhancement of safety and accuracy of the catheter treatment.

The above-described first embodiment may be modified as in a first modification to a sixth modification described below. The first modification to the sixth modification are also applicable to embodiments described below. In the description below, substantially the same components as those in the above-described drawings are denoted by the same reference numerals and will not be described below in detail. Differences from the above-described drawings will mainly be described.

<First Modification>

Figure 6:
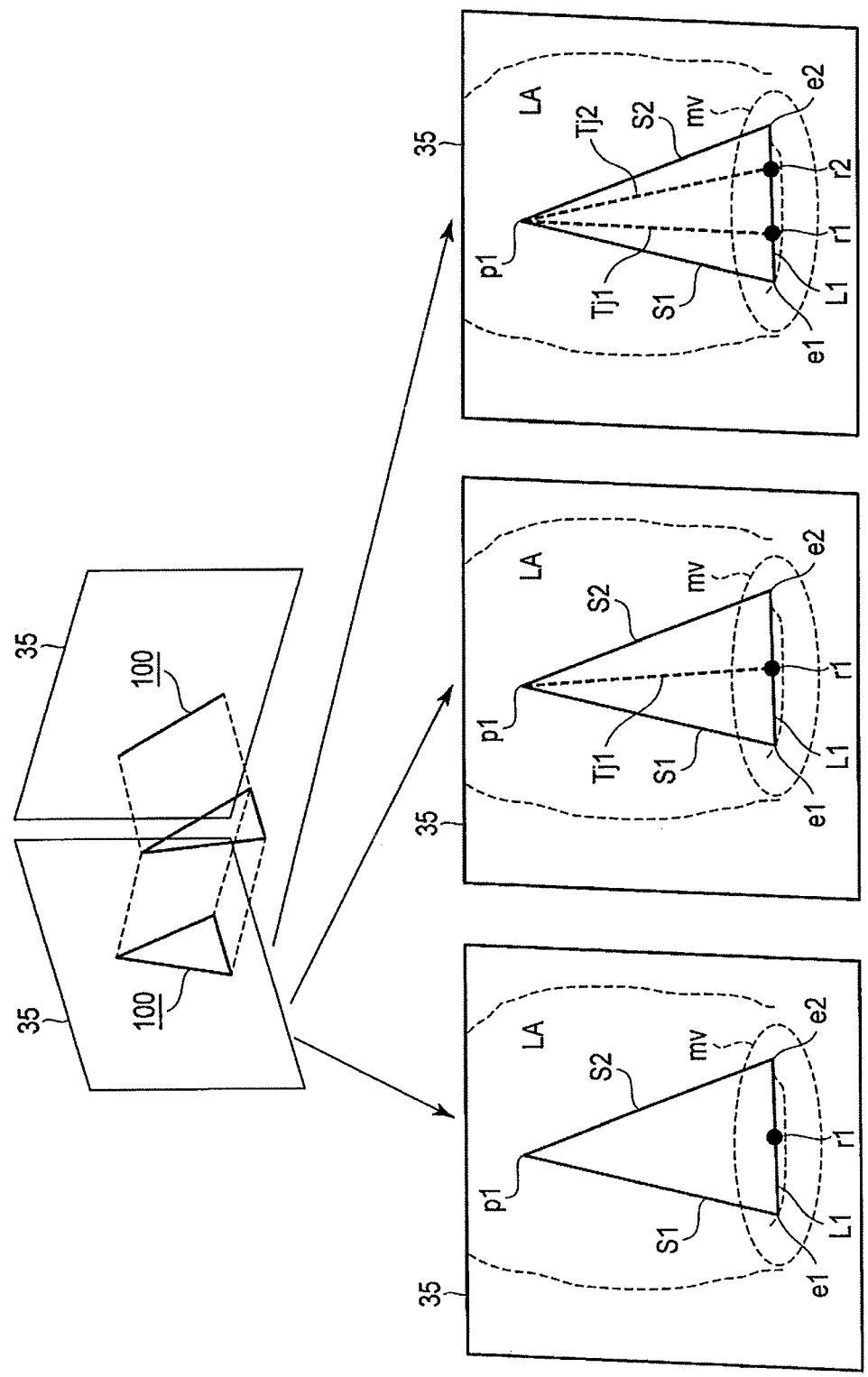
FIG. 6 is a schematic diagram depicting a navigation graphic in a first modification of the first embodiment.

In a first modification, the navigation graphic 100 denotes the back-flow position; FIG. 6 illustrates three examples. A lower left side of FIG. 6 illustrates an example where a first back-flow position r1 is set on the valve boundary line L1. A lower middle side of FIG. 6 illustrates an example where a trajectory Tj1 connecting the first back-flow position r1 and the puncture point p1 together is generated. A lower right side of FIG. 6 illustrates an example where a first and a second back-flow positions r1, r2 are set and where trajectories Tj1 and Tj2 are generated.

In this regard, in addition to performing the above-described function, the setting function 371 of the processing circuitry 37 sets at least one back-flow position r1 in the heart valve, on the valve boundary line L1.

In addition to performing the above-described functions, the graphic generation function 372 updates the valve boundary line L1 such that the valve boundary line L1 comprises a graphic depicting the back-flow position r1 and generates a navigation graphic 100 comprising the updated valve boundary line L1 and the safety lines S1, S2. As the graphic depicting the back-flow position r1, a circle is used in FIG. 6. However, the first modification is not limited to this. Any graphic such as a quadrangle or a star shape may be used. The graphic generation function 372 may set at least one back-flow position r1 in the heart valve, on the valve boundary line L1, connect the back-flow position r1 and the puncture point p1 together to further generate at least one trajectory Tj1 for the tip of the catheter 101, and generate a navigation graphic 100 further comprising the trajectory Tj1. The trajectory Tj1 generated is similar to the trajectory defined as the substantially overlapping safety lines S1, S2 in FIG. 3, but is very accurate in that the trajectory Tj1 allows the tip of the catheter 101 to be also guided between the safety lines S1, S2. In addition, the back-flow position is fairly infrequently located close to one end of the valve boundary line L1 instead of lying at the center of the valve boundary line L1. In some cases, a plurality of back-flow positions may be present. In any of these cases, the trajectory in the first modification allows the tip of the catheter 101 to be guided to the back-flow position. If the trajectory Tj1 is generated, the back-flow position r1 can be viewed as an intersection point between the trajectory Tj1 and the valve boundary line L1, enabling the graphic depicting the back-flow position r1 to be omitted.

When a plurality of back-flow positions r1, r2 are set, the graphic generation function 372 executes an update process of updating the trajectories Tj1, Tj2 such that each of trajectories Tj1, Tj2 connects the tip of the catheter 101 passing through the puncture point p1 to one of the plurality of back-flow positions r1, r2 according to the advancement of the tip. The graphic generation function 372 repeatedly executes the update process until the clip 102 is deployed at all of the back-flow positions r1, r2.

The remaining part of the configuration is similar to the corresponding part in the first embodiment.

Figure 7:
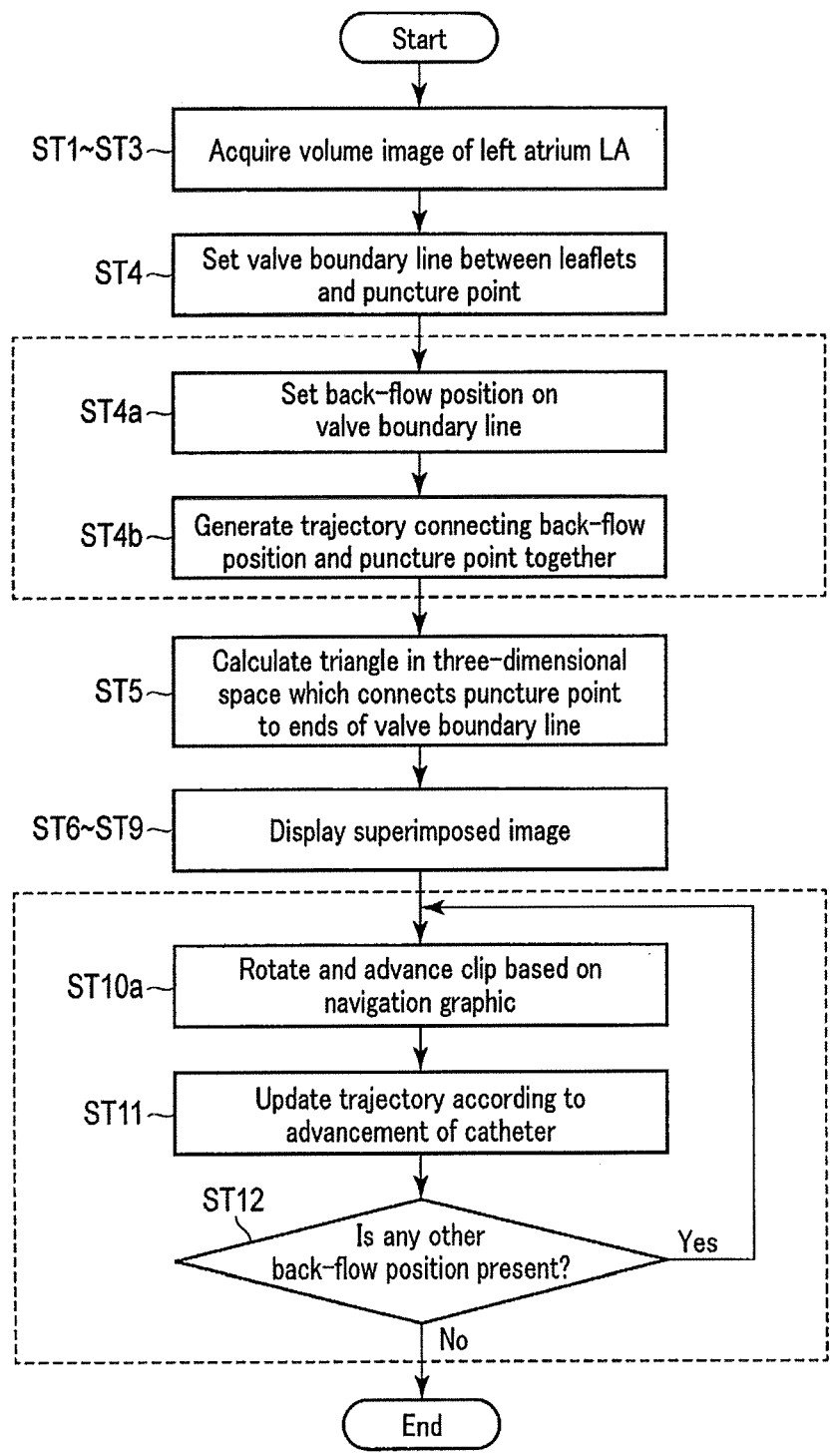
FIG. 7 is a flowchart illustrating operations of the X-ray diagnosis apparatus according to the first modification.

Now, operations of the X-ray diagnosis apparatus according to the first modification configured as described above will be described below using a flowchart in FIG. 7. The following description will be given with reference to a lower right one of three examples in FIG. 6. The cardiac chamber is the left atrium, and the heart valve is the mitral valve. The inner wall of the heart chamber is the atrial septum. The tip of the catheter 101 detachably holds the clip that clips the leaflets at the back-flow position.

Steps ST1 to ST3 are assumed to have been executed as described below with a volume image of the left atrium LA saved to the memory 31.

Furthermore, step ST4 is similarly assumed to be executed, and the setting function 371 of the processing circuitry 37 are assumed to have set the valve boundary line L1 between the leaflets of the mitral valve my and the puncture point p1 of the catheter 101 in the atrial septum, in accordance with an operation of the input interface 33.

Then, in step ST4a, the setting function 371 sets the two back-flow positions r1, r2 in the mitral valve mv, on the valve boundary line L1.

In step ST4b, the graphic generation function 372 connects the set two back-flow positions r1, r2 and the puncture point p1 together to generate two trajectories Tj1, Tj2 for the tip of the catheter 101.

Step ST5 to step ST9 are executed as described above, and the display 35 displays a superimposed image with the navigation graphic 100 superimposed on a fluoroscopic image. However, the navigation graphic 100 generated in step ST7 comprises the back-flow positions r1, r2 and the trajectories Tj1, Tj2. Thus, the navigation graphic 100 in the superimposed image comprises the back-flow positions r1, r2 and the trajectories Tj1, Tj2.

In step ST10a, the operator advances the clip 102 installed at the tip of a catheter 101 while referencing the navigation graphic 100 for two directions displayed on the display 35.

A plurality of back-flow positions r1, r2 are assumed to be set in step ST11. At this time, the graphic generation function 372 executes an update process of updating the trajectories Tj1, Tj2 such that each of the trajectories Tj1, Tj2 connects the tip of the catheter 101 passing through the puncture point p1 to one of the plurality of back-flow positions r1, r2 according to the advancement of the tip. Consequently, the clip 102 can be smoothly guided to one back-flow position r1 on the valve boundary line L1. The operator advances the clip 102 from the back-flow position r1 to the left atrium LA, clips the leaflets using the clip 102, then deploys the clip 102, and removes the tip of the catheter 101 through the puncture point p1.

In step ST12, the graphic generation function 372 repeatedly executes the update process until the clip 102 is deployed at all of the back-flow positions r1, r2. Specifically, the graphic generation function 372 determines whether or not any trajectory Tj1 remains non-updated to determine whether or not any remaining back-flow position r2 is present where the clip 102 has not been deployed. If the result of the determination indicates that any remaining back-flow position r2 is present, the process returns to step ST10a. When the processing in step ST10a to step ST12 is repeatedly executed, burdens on the object P are minimized by using the present puncture point p1.

If the result of the determination indicates that no remaining back-flow position r2 is present, the catheter treatment is completed when stoppage of a back flow through the mitral valve my of the object P (remedy of the mitral incompetence) is confirmed based on the ultrasonic doppler method.

According to the first modification as described above, at least one back-flow position in the heart valve is set on the valve boundary line, and the valve boundary line is updated so as to comprise a graphic depicting the back-flow position. A navigation graphic is generated which comprises the updated valve boundary line and the safety lines. This enables the same effects as those of the first embodiment to be produced and allows improvement of the accuracy with which the tip of the catheter is guided to the back-flow position.

Furthermore, at least one back-flow position in the heart valve is set on the valve boundary line, and the back-flow position and the puncture point are connected together to further generate at least one trajectory of the tip of the catheter. A navigation graphic further comprising a trajectory is generated. This allows further improvement of the accuracy with which the tip of the catheter is guided to the back-flow position.

When a plurality of back-flow positions are set, an update process is executed in which the trajectories are updated such that each of the trajectories connects the tip of the catheter passing through the puncture point to one of the plurality of back-flow positions according to the advancement of the tip. The update process is repeatedly executed until the clip is deployed at all of the back-flow positions. Consequently, if a plurality of back-flow positions are present, the accuracy of guiding the end of the catheter to each of the back-flow positions can be improved.

<Second Modification>

Figure 8:
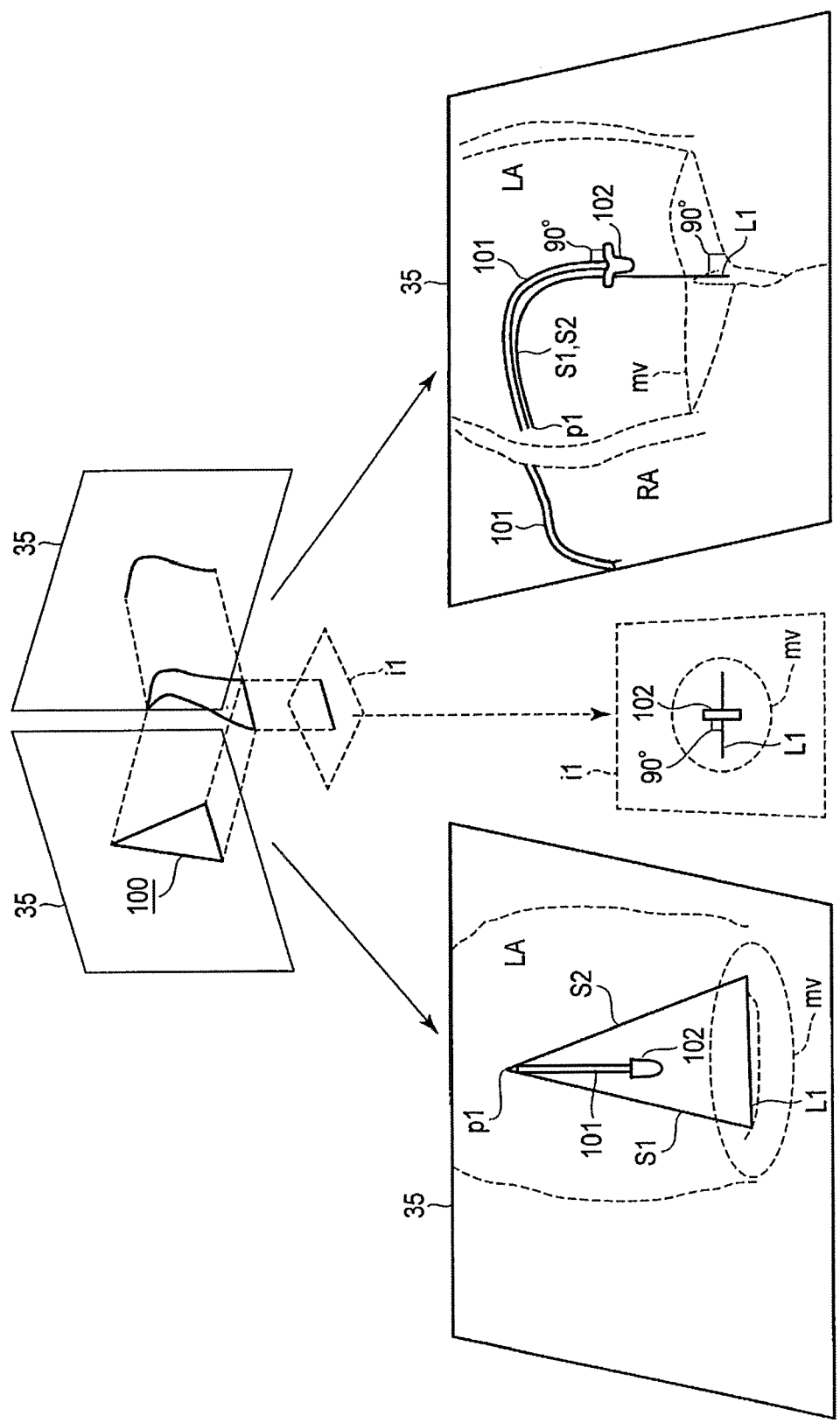
FIG. 8 is a schematic diagram depicting a navigation graphic in a second modification of the first embodiment.

A second modification is an aspect in which the safety lines S1, S2 in the navigation graphic 100 are curves, and an example is illustrated in FIG. 8. The navigation graphic 100 forms a curved surface enclosed by the plurality of safety lines S1, S2 and the valve boundary line L1. The navigation graphic 100 is a graphic in which three points connecting two of the plurality of safety lines S1, S2 and the valve boundary line L1 together form angles. As described above, the plurality of safety lines S1, S2 substantially overlap each other to indicate a trajectory of the catheter 101 when the second medical image is acquired in the first direction in which the projection area of the surface formed by the navigation graphic 100 is minimized. Similarly, each of the plurality of safety lines S1, S2 indicates the limit of the trajectory of the catheter 101 when the second medical image is acquired in the second direction in which the projection area of the surface formed by the navigation graphic 100 is maximized. As depicted in a lower right of FIG. 8, the navigation graphic 100 allows the clip 102 to be guided so as to be able to rush perpendicularly into the valve boundary line L1.

In this regard, the graphic generation function 372 of the processing circuitry 37 may automatically draw curves for the safety lines S1, S2. In this case, the graphic generation function 372 preferably detects the curvature of the catheter 101 in the right atrium RA, and based on the result of the detection, draw the curves for the safety lines S1, S2 connecting the puncture point p1 to the ends e1, e2 so as to reduce a variation in curvature. This is because the catheter 101 is a physical entity which does not suddenly bend or fold. Alternatively, the graphic generation function 372 may prompt the operator to operate the input interface 33 so as to draw the curves for the safety lines S1, S2 in accordance with the operation. In this case, the graphic generation function 372 prepares a plurality of curve patterns with a plurality of different curvatures so that the operator can select any of the plurality of curve patterns. Alternatively, the graphic generation function 372 may correct the curves for the safety lines S1, S2 drawn by the operator so as to reduce a variation in curvature with respect to the curvature of the catheter 101 in the right atrium RA.

The remaining part of the configuration is similar to the corresponding part in the first embodiment.

In the second variation as described above, the navigation graphic 100 forms a curved surface enclosed by the plurality of safety lines S1, S2 and the valve boundary line L1. In addition to allowing the same effects as those of the first embodiment to be produced, the second modification enables the tip of the catheter to be guided so as to rush perpendicularly into the valve boundary line by using curves as the plurality of safety lines. Therefore, the modification allows safety and accuracy of the catheter treatment to be further improved.

<Third Modification>

A third modification is an aspect for display settings other than the shape, such as the color, line type, and display on/off of the navigation graphic 100.

In this regard, the memory 31 stores a setting table 31T which can be updated in accordance with an operation of the input interface 33, for example, as depicted in FIG. 9.

The setting table 31T stores image names, control targets, selections, and flags in association with each other. For the image name, for example, the "navigation graphic", the "volume image", and the like may be used as needed. For the control target, for example, the "color", the "line type", "display", and the like may be used as needed. For the selection, for example, "stark white", "pitch black", "multiple colors", and the like may be used as needed. For the "multiple colors", particular colors may be set by default, or the colors may be set to vary at time intervals. For the flag, select "1", unselect "0", and the like may be used as needed.

In addition to performing the above-described functions, the graphic generation function 372 generates a navigation graphic 100 with the color or the line type thereof adjusted.

In addition to performing the above-described function, the superimposed image generation function 373 further superimposes a volume image to generate a superimposed image based on the setting table 31T.

The remaining part of the configuration is similar to the corresponding part in the first embodiment.

In the third modification described above, the superimposed image is generated based on the setting table, which stores the image names, the control targets, the selections, and the flags in association with one another. Consequently, in addition to producing the same effects as those of the first embodiment, the third modification allows the navigation graphic and the volume image to be displayed so as to be easily visible according to the operator's preferences.

For example, when the navigation graphic 100 is displayed on a fluoroscopic image, the lines may be displayed in stark white, pitch black, or multiple colors. The lines in the navigation graphic 100 may be adjustably set to be solid lines, dotted lines, or the like. Display of the navigation graphic 100 may be adjustably turned on or off. A superimposed image with a volume image projected thereon and the navigation graphic 100 may be displayed on the fluoroscopic image at the same time. Consequently, the mitral valve mv, which is not visible on the fluoroscopic image, is visible on the volume image. Display of the navigation graphic 100 and the volume image may be individually controllably turned on or off.

<Fourth Modification>

The fourth modification is an aspect for rotational display of the navigation graphic 100.

In this regard, in addition to performing the above-described functions, the graphic generation function 372 generates a navigation graphic 100 with a rotation angle corresponding to the angles of the arms 91, 191 indicated by the first relative position and the second relative position in the memory 31.

The remaining part of the configuration is similar to the corresponding part in the first embodiment.

In the fourth modification as described above, the navigation graphic 100 is generated so as to have a rotation angle corresponding to the angles of the arms 91, 191. The fluoroscopic image is acquired in real time according to the angles of the arms 91, 191. Thus, according to rotations of the arms 91, 191, the superimposed image is generated by superimposing the rotated navigation graphic 100 on the rotated fluoroscopic image. Therefore, in addition to producing the same effects as those of the first embodiment, the fourth variation allows the navigation graphic 100 to be rotationally displayed according to the rotations of the arms 91, 191.

<Fifth Modification>

A fifth modification is an aspect for display control with a variation in shape in which the navigation graphic for each cardiac phase is switched in synchronism with heart beat movement. In this regard, the fifth modification uses the electrocardiograph 43 depicted in FIG. 2. Based on an electrocardiographic waveform signal from the electrocardiograph 43, a volume image is acquired for each cardiac aspect.

In addition to performing the above-described function, the setting function 371 of the processing circuitry 37 sets the valve boundary line L1 and the puncture point p1 in the volume image for each cardiac phase.

The graphic generation function 372 generates a navigation graphic 100 for each cardiac phase by generating a plurality of safety lines S1, S2 for each cardiac phase based on the valve boundary line L1 and the puncture point p1 set for each cardiac phase.

The superimposed image generation function 373 generates a superimposed image by superimposing, in synchronism with the heart beat movement, the navigation graphic 100 for the corresponding cardiac phase on the fluoroscopic image based on the electrocardiographic waveform signal from the electrocardiograph 43.

The remaining part of the configuration is similar to the corresponding part in the first embodiment.

The fifth modification as described above generates a navigation graphic for each cardiac phase to generate a superimposed image comprising the navigation graphic 100 for the corresponding cardiac phase in synchronism with the heart beat movement. Consequently, the navigation graphic can be displayed in synchronism with the heart beat movement.

<Sixth Modification>

Figure 10:
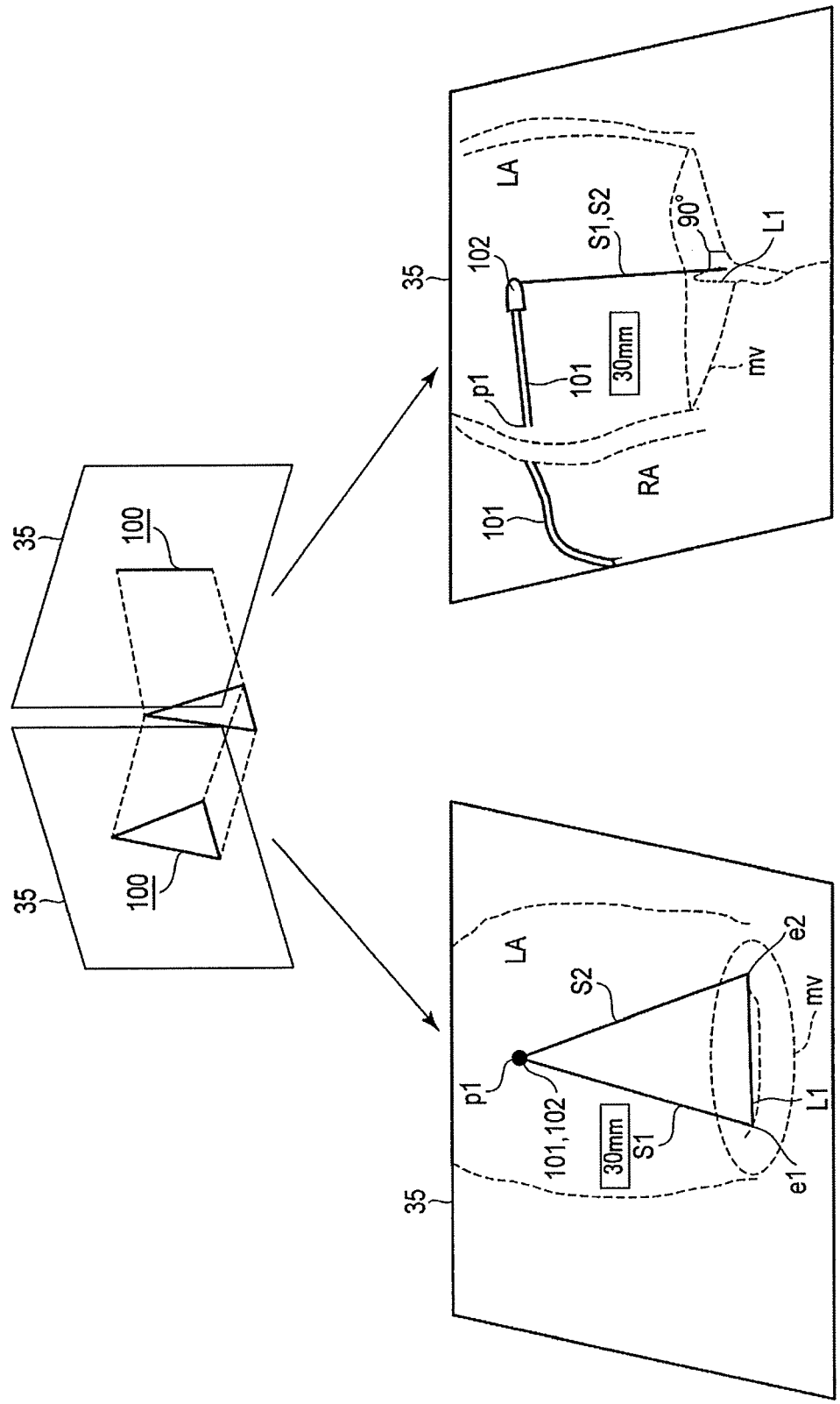
FIG. 10 is a schematic diagram depicting a navigation graphic in a sixth modification of the first embodiment.
Figure 11:
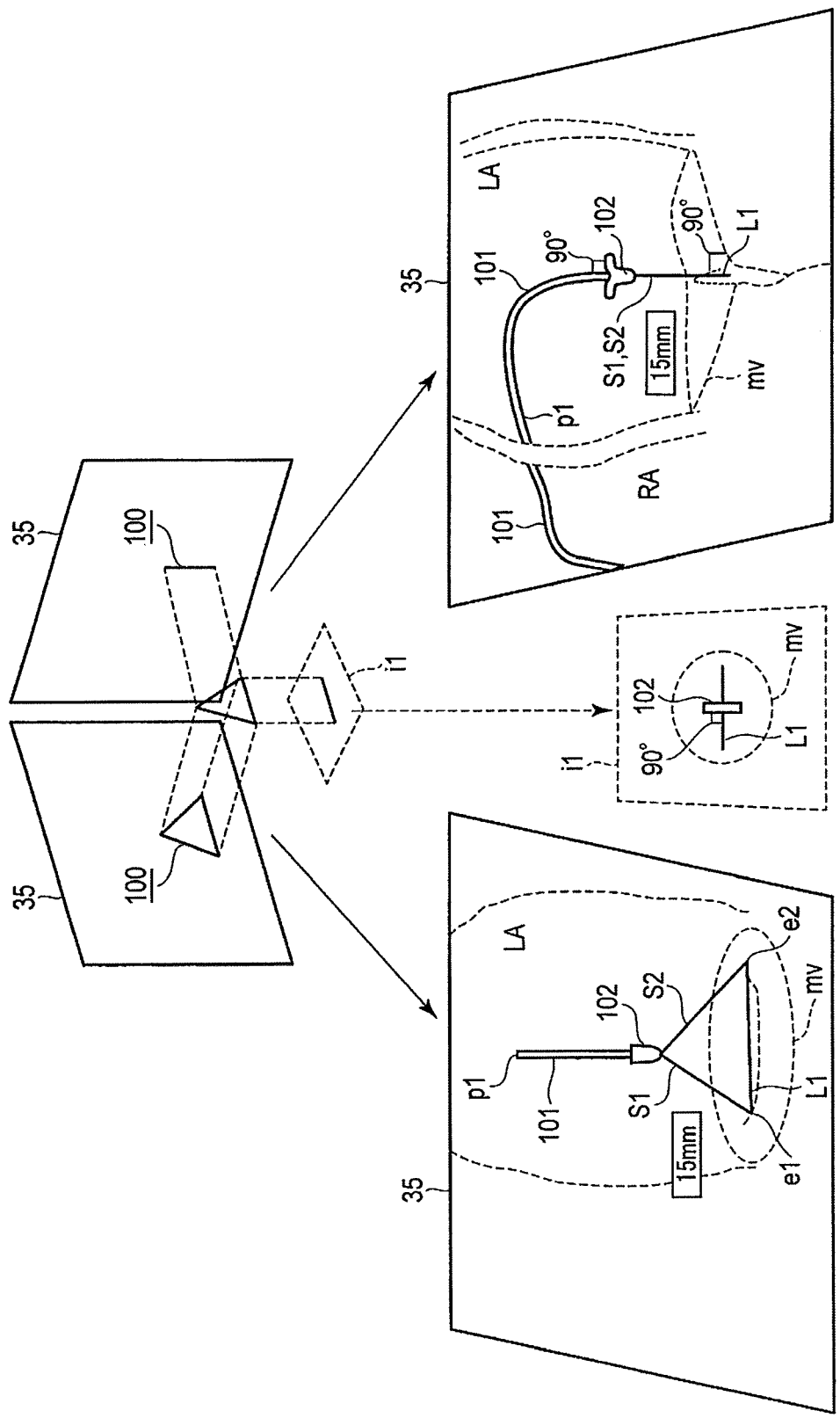
FIG. 11 is a schematic diagram depicting a navigation graphic in a sixth modification of the first embodiment.

A sixth modification is an aspect where the navigation graphic 100 is updated according to the advancement of the tip of the catheter 101 as depicted in FIG. 10 and FIG. 11.

In this regard, after, on the superimposed image, the catheter 101 is stuck into the inner wall, the graphic generation function 372 updates the navigation graphic 100 by updating the plurality of safety lines S1, S2 such that the safety lines S1, S2 individually connect the tip of the catheter 101 which replaces the puncture point p1 to the ends e1, e2 of the valve boundary line L1.

In addition to updating the navigation graphic 100, the graphic generation function 372 may numerically display the distance between the tip of the catheter 101 and the valve boundary line L1 in millimeters. The distance may be a distance between the tip of the catheter 101 and a central position of the valve boundary line L1 or a distance between the tip of the catheter 101 and a designated position on the valve boundary line L1. The designated position may be a back-flow position designated by an operation of the input interface 33.

The remaining part of the configuration is similar to the corresponding part in the first embodiment.

In the sixth modification as described above, after, on the superimposed image, the catheter is stuck into the inner wall, the navigation graphic is updated by updating the plurality of safety lines such that the safety lines individually connect the tip of the catheter which replaces the puncture point to the ends of the valve boundary line. Therefore, in addition to producing the same effects as those of the first embodiment, the sixth modification varies the navigation graphic according to the distance over which the catheter has advanced and the remaining distance.

In addition, the processing circuitry 37 senses the tip of the catheter 101 and updates the navigation graphic 100 according to the advancement of the tip of the catheter 101. Consequently, the operator's confidence can further be improved.

The processing circuitry 37 can sense the tip of the catheter 101 to evaluate the distance from the root of the clip 102 installed at the tip of the catheter 101 to the valve boundary line L1. Consequently, the operator's confidence can further be improved.

Second Embodiment

A second embodiment relates to an aspect where volume data on the object P is acquired before a procedure of a catheter treatment is started.

In most cases, a volume image (3D data) is acquired before the procedure is started. The volume image may be image data based on any of CT, magnetic resonance imaging (MRI), transthoracic echocardiography (TTE), and transesophageal echocardiography (TEE). Typically, CT data or TEE data is often acquired as a volume image. When a volume image is acquired, the valve boundary line L1 and the safety lines S1, S2 in the three-dimensional space can be generated before the procedure is started. Before the procedure is started, registration of the volume image and the fluoroscopic image is executed, and after misalignment is eliminated, the navigation graphic 100 is superimposed on the fluoroscopic image.

In this regard, in addition to performing the above-described functions, the superimposed image generation function 373 has a function to register the volume data (first medical image) and the fluoroscopic image (second medical image) in the memory 31.

The graphic generation function 372 updates the puncture point p1 in the three-dimensional space so as to eliminate the misalignment between the puncture point p1 in the three-dimensional space calculated before the procedure is started and a puncture point p1x (not depicted in the drawings) detected in the fluoroscopic image after the registration. Specifically, the graphic generation function 372 updates the navigation graphic 100 by updating the plurality of safety lines S1, S2 such that the safety lines S1, S2 individually connect the puncture point pix which replaces the puncture point p1 to the ends e1, e2 of the valve boundary line L1.

The remaining part of the configuration is similar to the corresponding part in the first embodiment.

Figure 12:
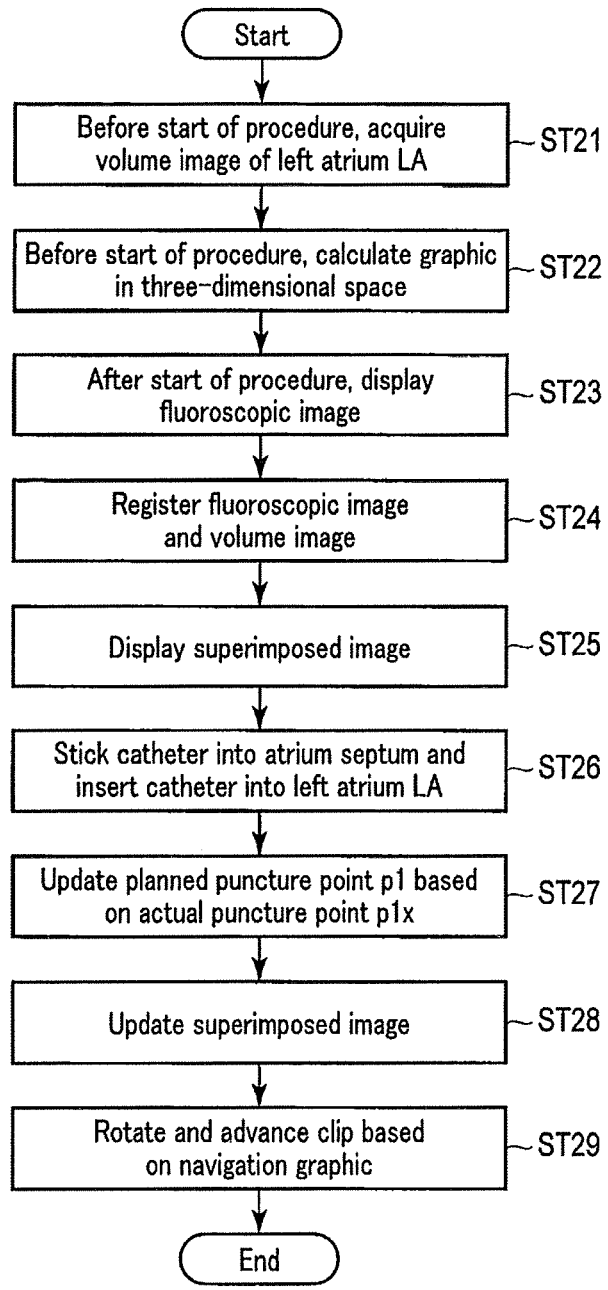
FIG. 12 is a flowchart illustrating operations in a second embodiment.

Operations of the X-ray diagnosis apparatus configured as described will be described using a flowchart in FIG. 12.

In step ST21 before the procedure, a volume image of the left atrium LA is acquired and saved to the memory 31 as is the case with step ST1 to step ST3 described above.

In step ST22 before the procedure, the processing circuitry 37 of the image processing apparatus 30 displays the volume image saved in the memory 31 on the display 35. The setting function 371 sets the valve boundary line L1 between the leaflets of the mitral valve my in the left atrium LA and the puncture point p1 planned before the procedure in accordance with an operation of the input interface 33 by the operator.

The graphic generation function 372 calculates a graphic in the three-dimensional space which connects the planned puncture point p1 to the ends e1, e2 of the valve boundary line L1 with the safety lines S1, S2. The graphic resulting from the calculation is superimposed on the volume image and saved to the memory 31 along with the volume image.

Now, the procedure is started. In step ST23 after the procedure is started, with the C arm 91 and the Ω arm 191 remaining stationary, the X-ray diagnosis apparatus 1 performs X-ray imaging. At this time, the X-ray diagnosis apparatus 1 emits the first X-ray and the second X-ray to the cardiac area of the object P in the orthogonal directions to generate fluoroscopic images based on outputs from the first X-ray detector 7 and the second X-ray detector 17. The first X-ray and the second X-ray may be radiated at the same time, or either one of the X-rays may be emitted, as described above. In either way, the fluoroscopic images generated are saved to the memory 31 and displayed on the display 35.

In step ST24, the superimposed image generation function 373 registers the fluoroscopic image being displayed and the volume image on which the graphic resulting from the calculation is superimposed.

In step ST25, the graphic generation function 372 generates a navigation graphic 100 by projecting the graphic in the three-dimensional space calculated in step ST22, on a two-dimensional plane. The superimposed image generation function 373 generates a superimposed image by superimposing the navigation graphic 100 on the fluoroscopic image. The display control function 374 allows the display 35 to display the superimposed image.

In step ST26, while referencing the superimposed image, the operator punctures the atrium septum and advances the catheter 101 from the right atrium RA to the left atrium LA. At this time, misalignment may occur between the puncture point p1 on the atrium septum calculated during planning and the actual puncture point p1x.

In step ST27, the graphic generation function 372 updates the coordinates of the planned puncture point p1 so as to eliminate the misalignment between the planned puncture point p1 and the puncture point p1x detected in the fluoroscopic image in the superimposed image after registration. The ends e1, e2 of the valve boundary line L1 are not detected. The fluoroscopic image is a 2D image and the puncture point p1 is in the three-dimensional space, and thus, strict update is precluded but update can be achieved with an accuracy enough to inhibit practical problems.

In step ST28, the graphic generation function 372 updates the navigation graphic 100 based on the updated puncture point p1. The superimposed image generation function 373 updates the superimposed image by superimposing the navigation graphic 100 on the fluoroscopic image. The display control function 374 allows the updated superimposed image to be displayed on the display 35.

In step ST29, processing similar to the processing in step ST10 described above is executed.

As described above, the second embodiment eliminates the need for a step of acquiring a volume image by 3D imaging using the contrast agent in step ST1 to step ST3. Thus, in addition to producing the same effects as those of the first embodiment and each modification, the second embodiment can reduce the needed time and the amount of contrast agent.

Third Embodiment

A third embodiment is an aspect corresponding to a modification of the second embodiment and where the planned puncture point p1 is not updated.

In this regard, the function to update the planned puncture point p1 used in the second embodiment is omitted from the graphic generation function 372.

The remaining part of the configuration is similar to the corresponding part in the second embodiment.

Figure 13:
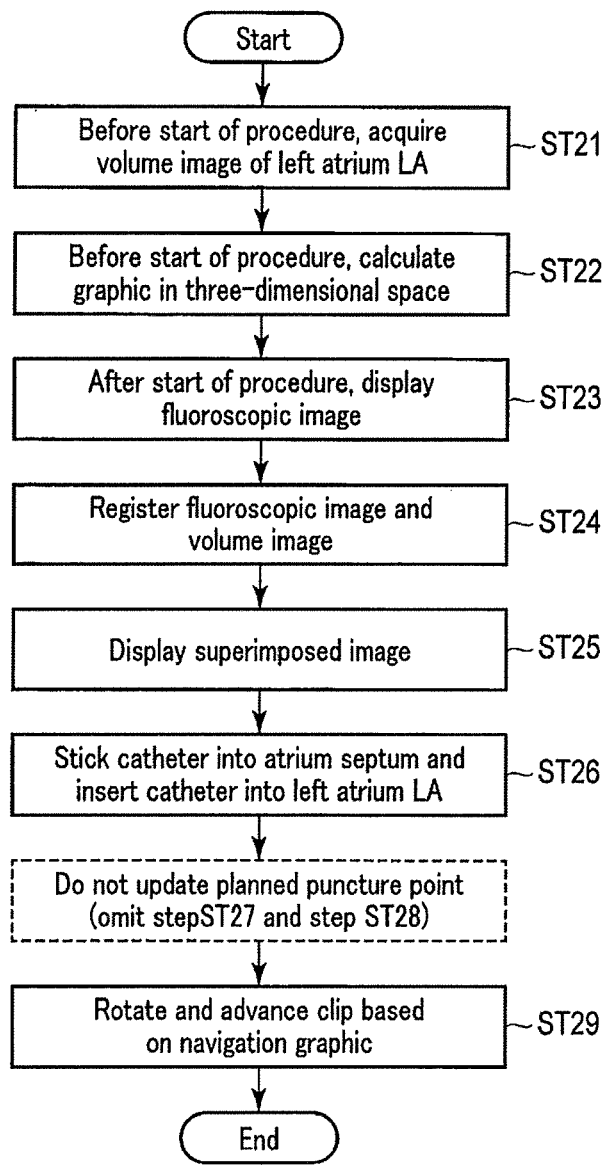
FIG. 13 is a flowchart illustrating operations in a third embodiment.

In the configuration as described above, step ST27 and step ST28 for update of the puncture point p1 are omitted, and step ST21 to step ST26 and step ST29 described above are executed, as depicted in FIG. 13.

At this time, a superimposed image is displayed in which the navigation graphic 100 based on the puncture point p1 planned before the procedure is started is superimposed on the fluoroscopic image. The operator executes a catheter treatment while referencing the superimposed image. Consequently, in addition to producing the same effects as those of the second embodiment, the third embodiment allows omission of the process of updating the puncture point p1, though the omission results in a reduced accuracy. The navigation graphic 100 may be displayed on a screen (window, monitor) different from a screen for the fluoroscopic image instead of being superimposed on the fluoroscopic image.

Fourth Embodiment

A fourth embodiment is an aspect corresponding to a modification of each of the first to third embodiments and where, instead of the volume image, a two-dimensional X-ray contrast image acquired in at least one direction is used to set the puncture point p1 and the valve boundary line L1. That is, instead of calculating a graphic such as a triangle in the three-dimensional space, the fourth embodiment defines a graphic connecting the puncture point p1 to the ends of the valve boundary line L1 in the two-dimensional space.

In this regard, the memory 31 stores at least one two-dimensional X-ray contrast image as a first medical image. In view of risk reduction, it is preferable to store a plurality of X-ray contrast images acquired in the respective directions as first medical images. The plurality of directions may be, for example, two directions or three directions.

The setting function 371 uses a two-dimensional X-ray contrast image as a first medical image during the above-described setting.

The graphic generation function 372 generates a plurality of safety lines S1, S2 individually connecting the puncture point p1 set on the two-dimensional X-ray contrast image to the ends e1, e2 of the valve boundary line to generate a navigation graphic 100 comprising the valve boundary line L1 and the safety lines S1, S2. As regards the graphic generation function 372, the navigation graphic 100 in the two-dimensional space may be a graphic enclosed by the valve boundary line L1 and the safety lines S1, S2 set on the two-dimensional X-ray contrast image for each imaging direction. That is, navigation graphics 100 may be individually generated for the respective imaging directions.

Alternatively, the graphic generation function 372 may execute calculation based on an epipolar theory using the valve boundary line L1 and the safety lines S1, S2 set on the two-dimensional X-ray contrast image for each imaging direction. In this case, the graphic generation function 372 calculates a graphic enclosed by the valve boundary line L1 and the safety lines S1, S2 in the three-dimensional space, and generates a navigation graphic 100 in which the calculated graphic is projected on the two-dimensional space. That is, the navigation graphic 100 may be generated by calculating a graphic in the three-dimensional space based on the plurality of imaging directions.

The remaining part of the configuration is similar to the corresponding part in each of the first to third embodiments.

Figure 14:
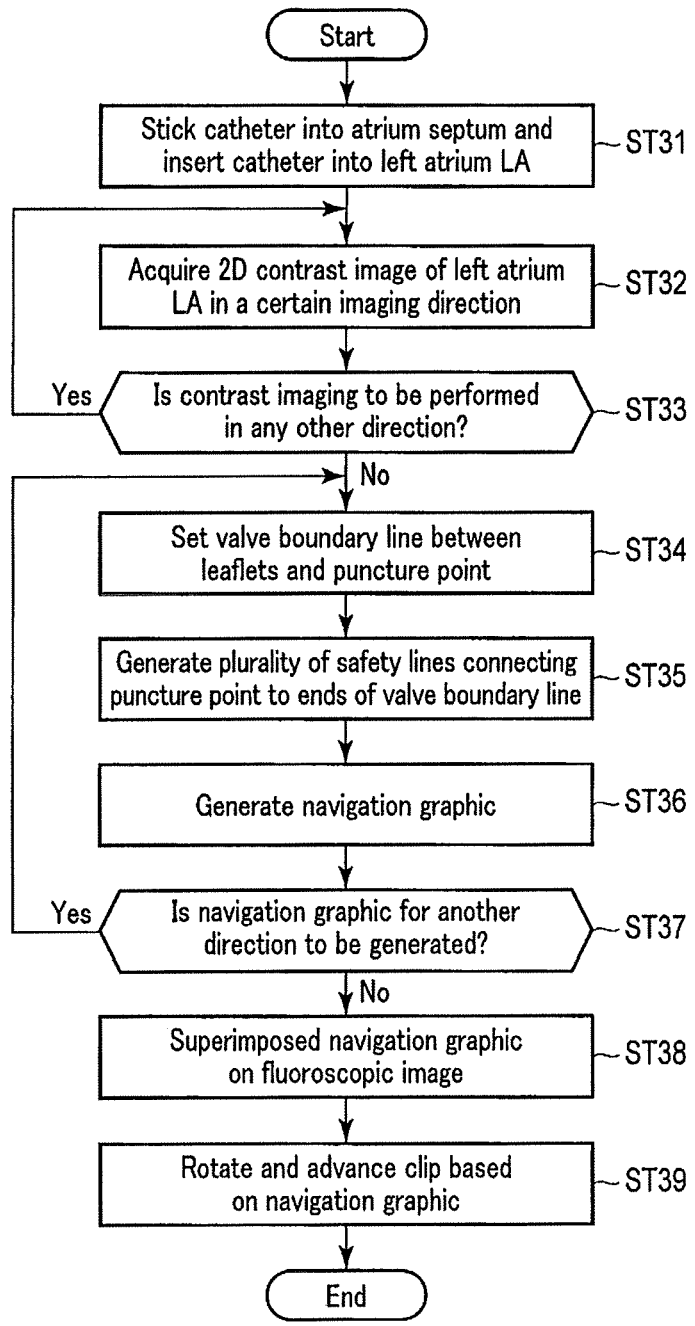
FIG. 14 is a flowchart illustrating operations in a fourth embodiment.

Now, operations of the X-ray diagnosis apparatus configured as described above will be described using a flowchart in FIG. 14.

In step ST31, while referencing a fluoroscopic image, the operator moves the catheter from the femoral vein of the object P to the right atrium RA, sticks (punctures) the catheter into the atrial septum, and inserts the catheter into the left atrium LA.

In step ST32, after the puncture, the X-ray diagnosis apparatus 1 performs, with the arms 91, 191 remaining stationary, digital angiography imaging to acquire a two-dimensional X-ray contrast image of the left atrium LA. The two-dimensional X-ray contrast image is saved to the memory 31.

In step ST33, if contrast imaging in another direction is performed, the C arm 91 is rotationally moved in the direction for the new imaging by an operation by the operator, and then, the X-ray diagnosis apparatus 1 re-executes step ST32. If contrast imaging in another direction is not performed, the process proceeds to step ST34. If only one direction is used, step ST33 is omitted.

In step ST34, the processing circuitry 37 of the image processing apparatus 30 reads a two-dimensional X-ray contrast image for a certain imaging direction from the memory 31 to allow the image to be displayed on the display 35. The setting function 371 sets the valve boundary line L1 between the leaflets of the mitral valve my in the left atrium LA and the puncture point p1 for the catheter 101 on the two-dimensional X-ray contrast image in accordance with an operation of the input interface 33 by the operator.

In step ST35 and step ST36, the graphic generation function 372 generates a plurality of safety lines S1, S2 connecting the puncture point p1 to the ends e1, e2 of the valve boundary line L1 to generate a navigation graphic 100 comprising the valve boundary line L1 and the safety lines S1, S2.

In step ST37, if a navigation graphic for another imaging direction is generated, step ST34 to step ST36 are re-executed for this direction. In step ST37, if a navigation graphic for another imaging direction is not generated, the process proceeds to step S38. If only one direction is used, step ST37 is omitted.

In step ST38, with the C arm 91 and the Ω arm 191 remaining stationary, the X-ray diagnosis apparatus 1 radiates the first X-ray to the cardiac area of the object P in a certain imaging direction, and generates a fluoroscopic image based on an output from the first X-ray detector 7. The superimposed image generation function 373 generates a superimposed image by superimposing the navigation graphic 100 on the fluoroscopic image. The display control function 374 allows the display 35 to display the superimposed image.

In step ST39, if the operator continues the procedure with the angle of the C arm 91 remaining unchanged, the operator can advance forward the clip 102 installed at the tip of the catheter 101 while referencing the navigation graphic 100. At this time, the imaging direction may be changed as needed so that the display 35 displays a superimposed image comprising the navigation graphic and the fluoroscopic image corresponding to the change. As described above, the rotation angle of the clip 102 may be adjusted. Then, the operator executes the procedure as described above to complete the catheter treatment.

As described above, the fourth embodiment can produce effects similar to those of the each of the first to third embodiments and each modification even when the two-dimensional X-ray contrast image is used as the first medical image.

Fifth Embodiment

A fifth embodiment is a modification of each of the first to fourth embodiments which uses transesophageal echocardiography (TEE).

For example, for a catheter treatment for the mitral valve, TEE is commonly used in which a tip of a TEE probe, an example of an ultrasonic probe, is inserted through the esophagus of the object to observe the heart and the like in vivo. If the TEE probe is fixed or a three-dimensional TEE is used, three-dimensional information can be acquired in real time.

In this regard, in the fifth embodiment, an ultrasonic diagnosis apparatus sets the puncture position p1 and the valve boundary line L1 in a TEE volume image, and generates a plurality of safety lines S1, S2 connecting the puncture position p1 to the ends of the valve boundary line L1 to generate a navigation graphic 100. The X-ray diagnosis apparatus 1 superimposes the navigation graphic 100 generated by the ultrasonic diagnosis apparatus on the fluoroscopic image to generate and display a superimposed image.

Figure 15:
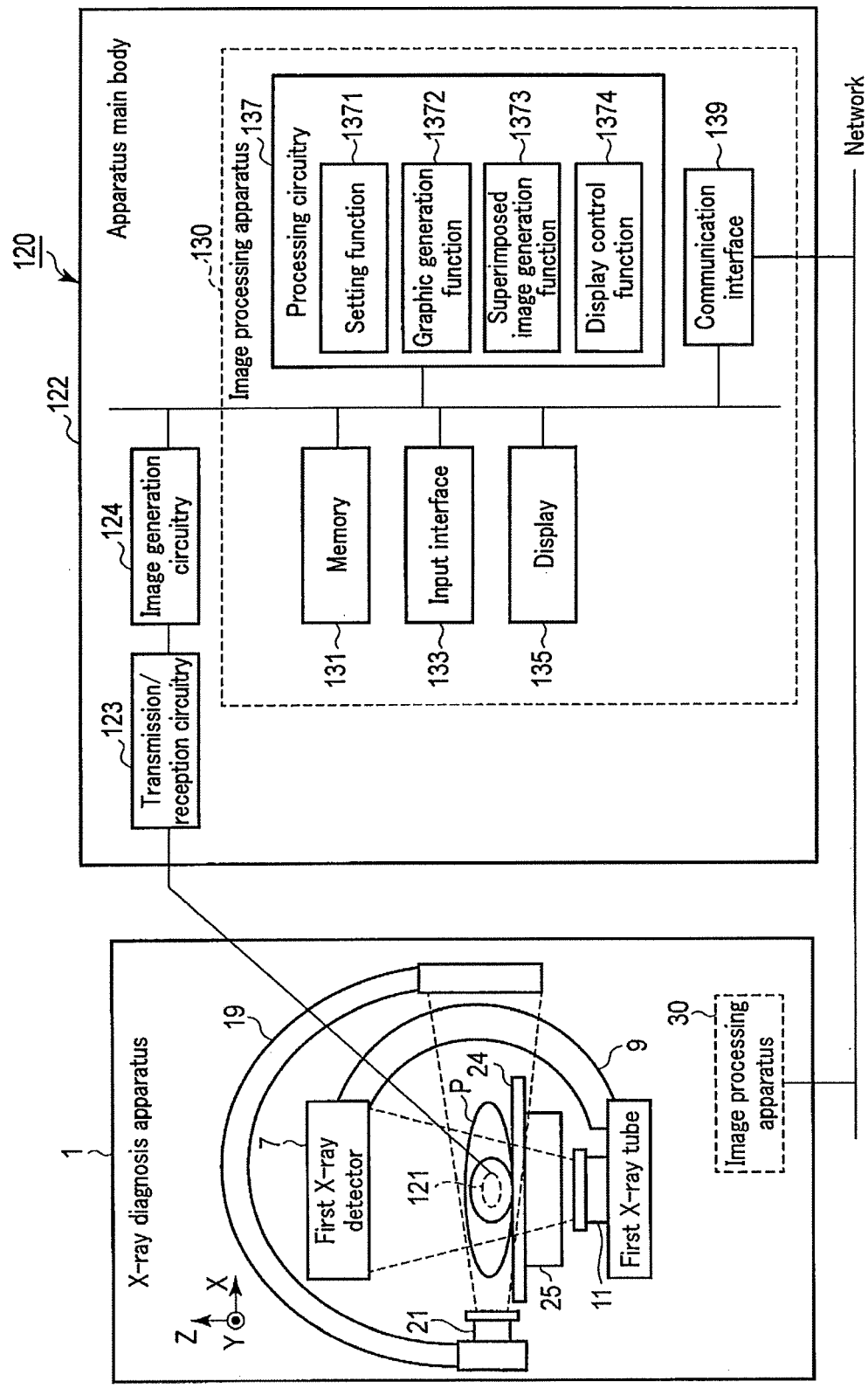
FIG. 15 is a block diagram illustrating an ultrasonic diagnosis apparatus according to a fifth embodiment and peripheral components therefor.

Specifically, as depicted in FIG. 15, an ultrasonic diagnosis apparatus 120 can communicate with the image processing apparatus 30 of the X-ray diagnosis apparatus 1 via the network.

The ultrasonic diagnosis apparatus 120 comprises an ultrasonic probe 121 and an apparatus main body 122. The apparatus main body 122 comprises transmission/reception circuitry 123, image generation circuitry 124, and the image processing apparatus 130. The image processing apparatus 130 comprises at least one of memory 131, an input interface 133, a display 135, processing circuitry 137, and a communication interface 139. The present embodiment is not limited to the image processing apparatus 130 provided in the ultrasonic diagnosis apparatus 120, and the image processing apparatus 130 may be provided as an external apparatus for the ultrasonic diagnosis apparatus 120.

The ultrasonic probe 121 is a transesophageal echocardiography (TEE) probe comprising a thin-tube-like tip portion at which a plurality of piezoelectric transducers are arranged and which is inserted through the esophagus of the object to transmit and receive ultrasonic waves in vivo. Incidentally, a description will be given on the assumption that one piezoelectric transducer constitutes one channel. The piezoelectric transducer generates ultrasonic, in response to a driving signal which is supplied from the transmission/reception circuitry 123. The piezoelectric transducer generates a reception echo signal, in response to reception of ultrasonic reflected by a biological tissue of a subject. The ultrasonic probe 121 may be a two-dimensional array probe in which a plurality of piezoelectric transducers is arranged in an azimuth direction (lateral direction) and an elevation direction. The 2D array TEE probe is electrically controlled to enable orthogonal slices of the heart to be observed at the same time.

Under the control by the processing circuitry 137, the transmission/reception circuitry 123 supplies driving signals to the respective piezoelectric transducers in the ultrasonic probe 121. The transmission/reception circuitry 123 generates a reception signal, based on reception echo signals which were generated by the respective piezoelectric transducers. Specifically, the transmission/reception circuitry 123 includes a pulse generator, transmission delay circuitry, pulser circuitry, a preamplifier, an analog-to-digital (hereinafter referred to as "A/D") converter, reception delay circuitry, and an adder, which are not illustrated.

The image generation circuitry 124 includes a B-mode processing unit and a Doppler processing unit, which are not illustrated. The B-mode processing unit includes an envelope detector and a logarithmic converter, which are not illustrated. The envelope detector executes envelope detection for the reception signal which was output from the transmission/reception circuitry 123. The envelope detector outputs the envelope-detected signal to the logarithmic converter (to be described later). The logarithmic converter subjects the envelope-detected signal to logarithmic conversion, and relatively emphasizes a weak signal. Based on the signal emphasized by the logarithmic converter, the B-mode processing unit generates a signal value (B-mode data) for each of depths in the transmission/reception of each scanning line and each ultrasonic.

A B-mode processing unit may generate three-dimensional B-mode data comprising a plurality of signal values arrayed in association with the lateral direction, the elevation direction, and a depth direction (hereinafter referred to as a range direction), respectively, in a scanned area. The range direction is the depth direction on scan lines. The three-dimensional B-mode data may be data comprising a plurality of pixel values or a plurality of brightness values arrayed in association with the lateral direction, the elevation direction, and the range direction, respectively, along the scan lines. Alternatively, the three-dimensional B-mode data may be data relating to a region of interest (hereinafter referred to as an ROI) preset in the scanned area. Alternatively, the B-mode processing unit may generate volume data instead of three-dimensional B-mode data. The data generated by the B-mode processing unit is collectively referred to as "B-mode data".

The Doppler processing unit includes a mixer, a low-pass filter, and a velocity/dispersion/power computing device, which are not illustrated. The mixer multiplies the reception signal, which was output from the transmission/reception circuitry 123, by a reference signal having a frequency f0 which is identical to the transmission/reception frequency. By this multiplication, a signal of a component of a Doppler shift frequency fd, and a signal including a frequency component of (2f0+fd) can be obtained. The low-pass filter eliminates the signal of the higher frequency component (2f0+fd) from between the signals including the two kinds of frequency components from the mixer. By eliminating the signal of the higher frequency component (2f0+fd), the Doppler processing unit generates a Doppler signal including the Doppler shift frequency fd. In the meantime, the Doppler processing unit may use a quadrature detection method in order to generate the Doppler signal. The Doppler signal is, for example, an echo component due to a blood flow, tissue, or contrast medium.

The velocity/dispersion/power computing device includes an MTI (Moving Target Indicator) filter and an autocorrelation computing unit, which are not illustrated. The MTI filter eliminates, from the generated Doppler signal, a Doppler component (clutter component) due to respiratory movement or pulsatory movement of an organ. The autocorrelation computing unit calculates an autocorrelation value for the Doppler signal in which only blood flow information was extracted by the MTI filter. Based on the calculated autocorrelation value, the autocorrelation computing unit calculates a mean velocity value of the blood flow, a dispersion value, and reflection power of the Doppler signal. The velocity/dispersion/power computing device generates color Doppler data, based on a mean velocity value of the blood flow based on plural Doppler signals, a dispersion value, and reflection power of Doppler signals. Hereinafter, the Doppler signal and color Doppler data are comprehensively referred to as "Doppler data".

In addition, the Doppler data and B-mode data are comprehensively referred to as "raw data". The raw data may be B-mode data by a high-frequency component of transmission ultrasonic in the echo signal, and elastic data relating to a biological tissue in the subject. The B-mode processing unit and Doppler processing unit output the generated raw data to a digital scan converter (hereinafter referred to as "DSC") which will be described later. The B-mode processing unit and Doppler processing unit may also output the generated raw data to a cine memory (not shown).

The image generation circuitry 124 includes a DSC (not shown). The image generation circuitry 124 executes a coordinate conversion process (resampling) on the DSC. The coordinate conversion process is a process of converting, for example, a scanning line signal sequence of ultrasonic scan, which is composed of raw data, to a scanning line signal sequence of a general video format, which is typified by television. The image generation circuitry 124 executes on the DSC an interpolation process following the coordinate conversion process. The Interpolation process is a process of interpolating data between scanning line signal sequences by using raw data in neighboring scanning line signal sequences.

By executing the coordinate conversion process and interpolation process on the raw data, the image generation circuitry 17 generates an ultrasonic image as a display image. Incidentally, the image generation circuitry 17 may include an image memory which stores data corresponding to the generated ultrasonic image. The image generation circuitry 17 synthesizes the generated ultrasonic image with character information and scale marks of various parameters. The ultrasonic image generated by using the B-mode data may be called "B-mode image". In addition, the ultrasonic image generated by using the Doppler data may be called "Doppler image". The ultrasonic volume image generated based on an output from the TEE probe may be called "TEE volume image".

The cine memory is a memory which stores, for example, ultrasonic images corresponding to a plurality of frames immediately before freeze. An ultrasonic motion image can also be displayed by successively displaying (cine display) images stored in this cine memory.

The memory 131 is composed of memories which store electrical information, such as a ROM (Read Only Memory), a RAM (Random Access Memory), an HDD (Hard Disk Drive) and an image memory, and peripheral circuitry accompanying these memories, such as a memory controller and a memory interface. The memory 131 stores a plurality of reception delay patterns with different focus depths, a control program of the present ultrasonic diagnosis apparatus, a diagnosis protocol, various kinds of data such as a transmission/reception condition, B-mode data, Doppler data, and B-mode images, Doppler images, and TEE volume images generated by the image generation circuitry 124.

The input interface 133 is realized by, for example, a trackball, switch buttons, a mouse, a keyboard, a touchpad which executes an input operation by a touch on an operation screen, and a touch panel display in which a display screen and a touchpad are integrated, these being configured to input to the apparatus main body 122 various instructions, commands, information, selection and settings from the operator. The input interface 133 is connected to the processing circuitry 137, converts an input operation, which was received from the operator, to an electric signal, and outputs the electric signal to the processing circuitry 137. In the meantime, in this specification, the input interface 133 is not limited to circuitry including physical operation components such as a mouse and a keyboard. Examples of the input interface 133 include electric signal processing circuitry which receives an electric signal corresponding to an input operation from an external input device provided separately from the apparatus, and outputs this electric signal to the processing circuitry 137.

The display 135 is controlled by the processing circuitry 137 to display the ultrasonic image, the navigation graphic, and the superimposed image. The display 135 comprises internal circuitry which supplies signals for display to a display main body and peripheral circuitry comprising a connector and a cable connected to the internal circuitry. The display displays various ultrasonic images generated by the image generation circuitry 124. In addition, the display 135 may execute, for the ultrasonic image generated by the image generation circuitry 124, adjustment of the brightness, contrast, dynamic range and γ correction, and allocation of a color map.

The processing circuitry 137 includes a processor and a memory, which are not illustrated. Based on a mode selection, a selection of a reception delay pattern list and the start/end of transmission, which were input by the operator via the input interface 133, the processing circuitry 137 reads out the transmission/reception condition and apparatus control program stored in the memory 131, and controls the main body of the ultrasonic diagnosis apparatus. For example, the processing circuitry 137 controls the transmission/reception circuitry 123 and image generation circuitry 124 according to the control program which was read out from the memory 131.

The processor of the processing circuitry 137 invokes and executes a program in the memory 131 to implement a setting function 1371, a graphic generation function 1372, a superimposed image generation function 1373, or a display control function 1374 corresponding to the program. As described above with reference to FIG. 15, the single processing circuitry 137 implements the setting function 1371, the graphic generation function 1372, the superimposed image generation function 1373, and the display control function 1374. However, the present embodiment is not limited to this. A plurality of independent processors may be combined together to form processing circuitry so that each of the processors executes the corresponding program to implement the corresponding function. The assignment of the setting function 1371, the graphic generation function 1372, the superimposed image generation function 1373, or the display control function 1374 is for convenience and can be changed as needed. For example, a setting process of the setting function 1371 may be executed by the graphic generation function 1372.

Figure 16:
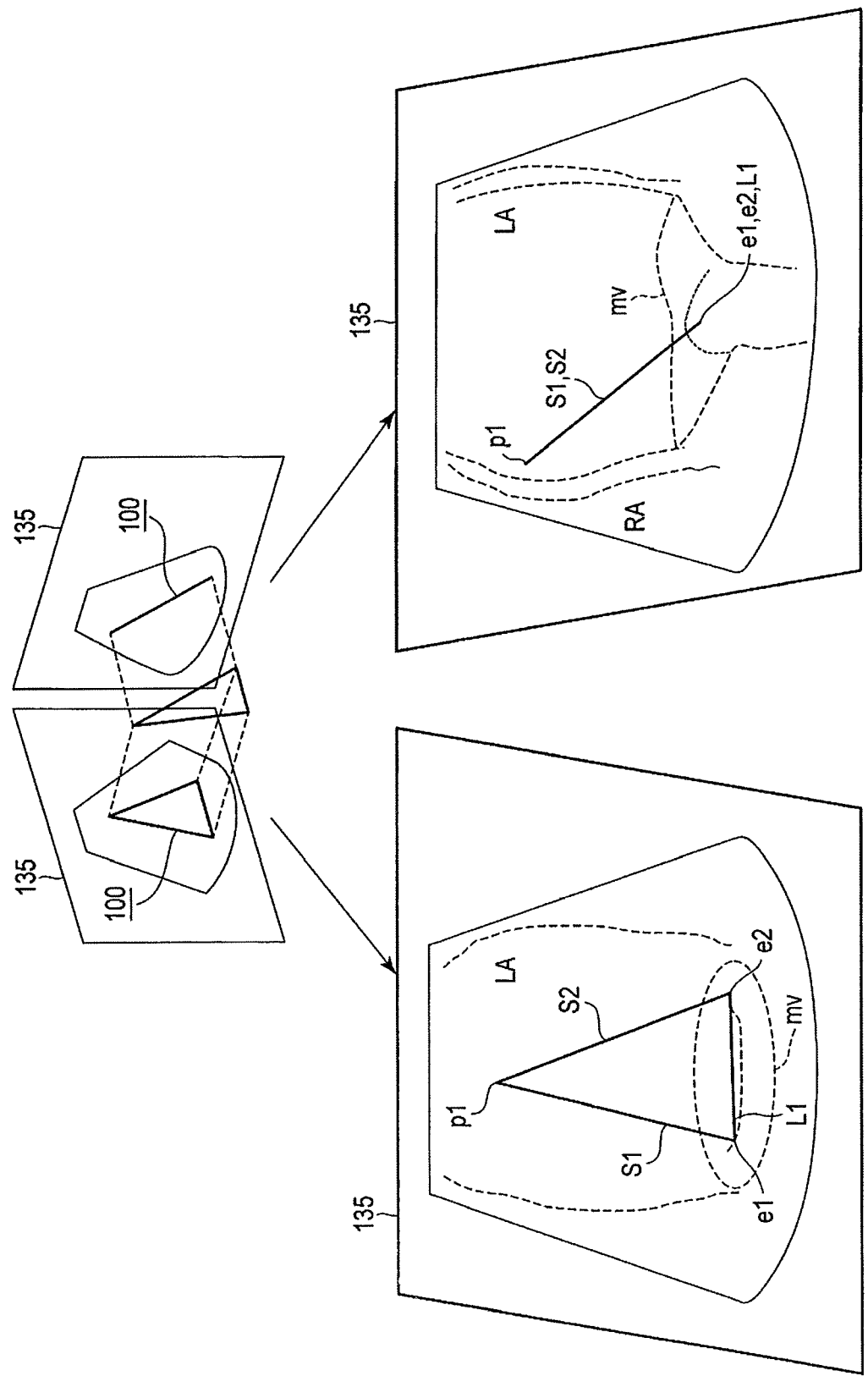
FIG. 16 is a schematic diagram illustrating a setting function in the fifth embodiment.

The setting function 1371 sets, based on the TEE volume image in the memory 131, each of the valve boundary line L1 indicating the boundaries between the leaflets of the heart valve in the cardiac chamber and the puncture point on the inner wall of the cardiac chamber through which the catheter is inserted. For example, as described above, the puncture point p1 and the plurality of ends e1, e2 at boundaries between the leaflets of a mitral valve my in the left atrium LA are assumed to be designated for the setting function 371 in accordance with operation of the input interface 133, as depicted in FIG. 16. In this case, the setting function sets the puncture point p1, and sets the boundary line L1 which is a straight line connecting the plurality of ends e1, e2 together.

The graphic generation function 1372 generates a plurality of safety lines S1, S2 individually connecting the puncture point p1 to the ends e1, e2 of the valve boundary line at a distance from the inner wall to generate a navigation graphic 100 comprising the valve boundary line L1 and the safety lines S1, S2. For example, when the puncture point p1 is designated in accordance with an operation of the input interface 133 by the operator, the graphic generation function 1372 generates a plurality of safety lines which are straight lines or curves connecting the puncture point to the plurality of ends of the valve boundary line. For example, when the puncture point and the curvature are designated, the graphic generation function 1372 generates a plurality of safety lines which are curves having the curvature and connecting the puncture point to the plurality of ends of the valve boundary line.

The graphic generation function 1372 may transmit a TEE volume image including the generated navigation graphic 100 to the X-ray diagnosis apparatus 1.

The superimposed image generation function 1373 superimposes the navigation graphic on the ultrasonic image to generate a superimposed image. The display control function 1374 allows the display 135 to display the superimposed image. However, the superimposed image generation function 373 and the display control function 374 are not used in the present embodiment but in modifications described below.

The communication interface 139 is a circuit which communicates with an external apparatus by wire, by radio, or by both. The external apparatus is, for example, a modality, the image processing apparatus, a server included in any of the radiological information system (RIS), the hospital information system, (HIS), and the picture archiving and communication system (PACS), or any other workstation.

Operations of the ultrasonic diagnosis apparatus and the X-ray diagnosis apparatus configured as described above will be described using a flowchart in FIG. 17. The object P is assumed to be laid on the top plate 24 of the X-ray diagnosis apparatus 1, and the tip of the ultrasonic probe 121, which serves as a TEE probe, is assumed to have been inserted through the esophagus.

In step ST41, while referencing a fluoroscopic image, the operator moves the catheter from the femoral vein of the object P to the right atrium RA, sticks (punctures) the catheter into the atrial septum, and inserts the catheter into the left atrium LA.

In step ST42 and step ST43, the ultrasonic diagnosis apparatus 120 performs three-dimensional imaging by means of TEE based on an output from the ultrasonic probe 121. Consequently, the ultrasonic diagnosis apparatus 120 acquires a TEE volume image of the left atrium LA of the object P. The TEE volume image is saved to the memory 131.

In step ST44, the processing circuitry 137 of the image processing apparatus 130 reads a TEE volume image from the memory 131 to allow the image to be displayed on the display 135. The setting function 1371 sets the valve boundary line L1 between the leaflets of the mitral valve my in the left atrium LA and the puncture point p1 for the catheter, on the TEE volume image, in accordance with an operation of the input interface 133 by the operator.

In step ST45 and step ST46, the graphic generation function 1372 generates a plurality of safety lines S1, S2 connecting the puncture point p1 to the ends e1, e2 of the valve boundary line L1 to generate a navigation graphic 100 comprising the valve boundary line L1 and the safety lines S1, S2.

In step ST47, the graphic generation function 1372 allows the communication interface 139 to transmit the TEE volume image comprising the navigation graphic 100 to the X-ray diagnosis apparatus 1 via the network.

In step ST48, the image processing apparatus 30 of the X-ray diagnosis apparatus 1 allows the communication interface 39 to receive and save the TEE volume image to the memory 31.

In step ST49, the superimposed image generation function 373 of the image processing apparatus 30 reads the TEE volume image from the memory 31 and superimposes the navigation graphic 100 in the TEE volume image on the fluoroscopic image to generate a superimposed image. The display control function 374 allows the display 35 to display the superimposed image.

In step ST50, the operator can advance forward the clip 102 installed at the tip of the catheter 101 while referencing the navigation graphic 100, as described above. As described above, the rotation angle of the clip 102 may be adjusted. Then, the operator executes the procedure as described above to complete the catheter treatment.

As described above, even if the first medical image is an ultrasonic volume image, the second medical image is a fluoroscopic image, the ultrasonic diagnosis apparatus generates a navigation graphic, and the X-ray diagnosis apparatus generates a superimposed image, the fifth embodiment can produce effects similar to those of each of the first to fourth embodiments and each modification.

<Modification>

A modification of the fifth embodiment will be described.

The modification is an aspect corresponding to FIG. 15 from which the X-ray diagnosis apparatus is omitted. In the modification, the ultrasonic diagnosis apparatus 120 displays a superimposed image in which the navigation graphic is superimposed on the superimposed image.

In this regard, in the modification, the ultrasonic diagnosis apparatus 120 uses the superimposed image generation function 1373 and the display control function 1374 described above.

The remaining part of the configuration of the ultrasonic diagnosis apparatus 120 is similar to the corresponding part in the fifth embodiment.

Figure 18:
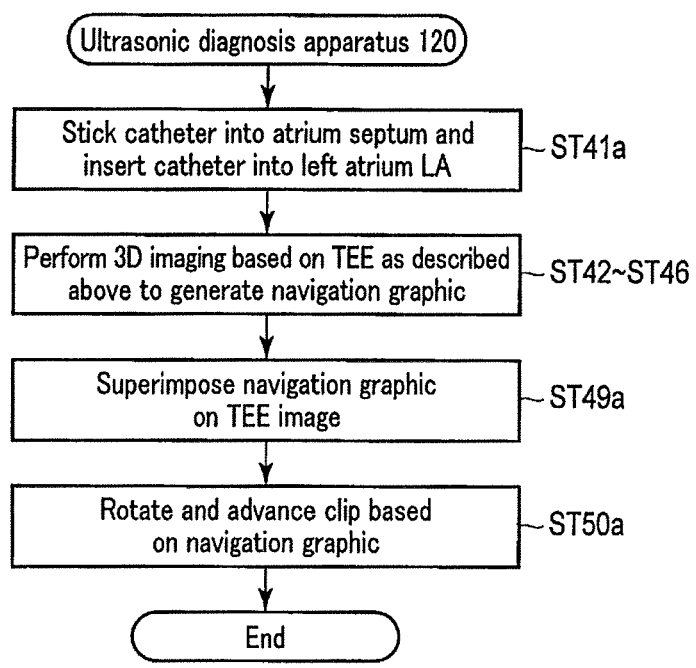
FIG. 18 is a flowchart illustrating operations of a modification of the fifth embodiment.

Operations of the ultrasonic diagnosis apparatus configured as described above will be described using a flowchart in FIG. 18. The object P is assumed to be laid on a bed not depicted in the drawings, and the tip of the ultrasonic probe 121, which serves as a TEE probe, is assumed to have been inserted through the esophagus.

In step ST41a, while referencing a TEE image, the operator moves the catheter from the femoral vein of the object P to the right atrium RA, sticks the catheter into the atrial septum, and inserts the catheter into the left atrium LA.

Then, step ST42 to step ST46 are executed as described above to generate a navigation graphic 100 on the TEE volume image. The TEE volume image is saved to the memory 131.

In step ST49a, the superimposed image generation function 1373 of the ultrasonic diagnosis apparatus 120 reads the TEE volume image from the memory 131 and superimposes the navigation graphic 100 in the TEE volume image on the TEE image to generate a superimposed image. The display control function 1374 allows the display 135 to display the superimposed image.

In step ST50a, while referencing the navigation graphic 100 on the TEE image, the operator can rotate and advance the clip 102 installed at the tip of the catheter 101 as described above. Then, the operator executes the procedure as described above to complete the catheter treatment.

As described above, even if the first medical image is an ultrasonic volume image, the second medical image is an ultrasonic image, and the ultrasonic diagnosis apparatus generates a navigation graphic and a superimposed image, the modification can produce effects similar to those of the fifth embodiment. The modification can also produce effects similar to those of each of the first to fourth embodiments and each modification, which effects correspond to the effects of the fifth embodiment.

That is, the ultrasonic diagnosis apparatus 120 displays the navigation graphic 100 in the TEE image instead of superimposing the navigation graphic 100 on the fluoroscopic image. While referencing the navigation graphic 100 on the TEE image, the operator can advance and rotate the clip 102 at the tip of the catheter 101. This also allows production of effects similar to those of each of the first to fifth embodiments and each modification.

Sixth Embodiment

A sixth embodiment is an aspect corresponding to a modification of each of the first to fifth embodiments and where in order to make the navigation graphic 100 easy to see, the arms 91, 191 are controlled based on the projection area of a surface formed by the navigation graphic 100.

Figure 19:
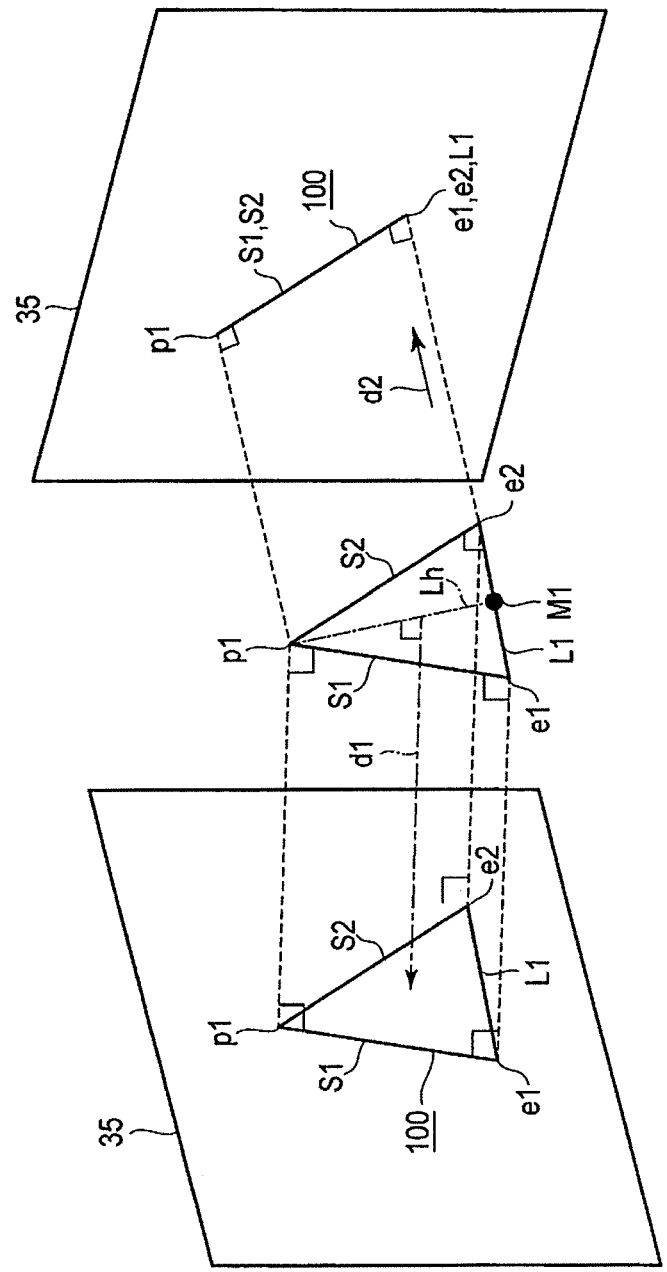
FIG. 19 is a schematic diagram illustrating an imaging direction in a sixth embodiment.

Specifically, as depicted in FIG. 19, after generating a navigation graphic 100 including the safety lines S1, S2 and the valve boundary line L1, the graphic generation function 372 delivers to the control circuitry 41 information indicating an imaging direction d1 in which the projection area of the surface formed by the navigation graphic 100 is maximized. The control circuitry 41 controls the position of the Ω arm 91 based on the information indicating the imaging direction d1. When the surface formed by the navigation graphic 100 is a triangle, a triangle on the three-dimensional space in the center of FIG. 19 is parallel to a triangle on the three-dimensional space in the left of FIG. 19. The imaging direction d1 as described above may be determined to be, for example, a direction which is perpendicular to the valve boundary line L1 and which is also perpendicular to a bisector Lh connecting a middle point M1 of the valve boundary line L1 to the puncture point p1. When the imaging direction d1 is determined from the valve boundary line L1 and the bisector Lh, the projection area of the surface formed by the navigation graphic 100 need not be determined. To determine the projection area, for example, the area of the triangle on the two-dimensional space in the left of FIG. 19 may be determined or the number of pixels enclosed by the triangle on the two-dimensional space may be counted.

The graphic generation function 372 delivers to the control circuitry 41 information indicating an imaging direction d2 which perpendicularly crosses the imaging direction d1 defined by the Ω arm 191. The control circuitry 41 controls the C arm 91 based on the information indicating the imaging direction d2. In this case, the imaging direction defined by the C arm 91 is a direction in which the projection area of the surface formed by the navigation graphic 100 is minimized. The triangle on the three-dimensional space in the center of FIG. 19 lies on the same plane as that of a straight line on the two-dimensional space in the right of FIG. 19. That is, the plane to which the graphic (triangle) on the three-dimensional space belongs is orthogonal to the plane to which the graphic (straight line) on the two-dimensional space belongs. The imaging direction d2 as described above may be determined to be, for example, a direction which is parallel to the valve boundary line L1. Similarly, when the imaging direction d2 is determined from the valve boundary line L1, the projection area of the surface formed by the navigation graphic 100 need not be determined. To determine the projection area, for example, the area of a substantially-straight-line-like triangle on the two-dimensional space in the right of FIG. 19 may be determined or the number of pixels enclosed by the substantially-straight-line-like triangle on the two-dimensional space may be counted.

Figure 20:
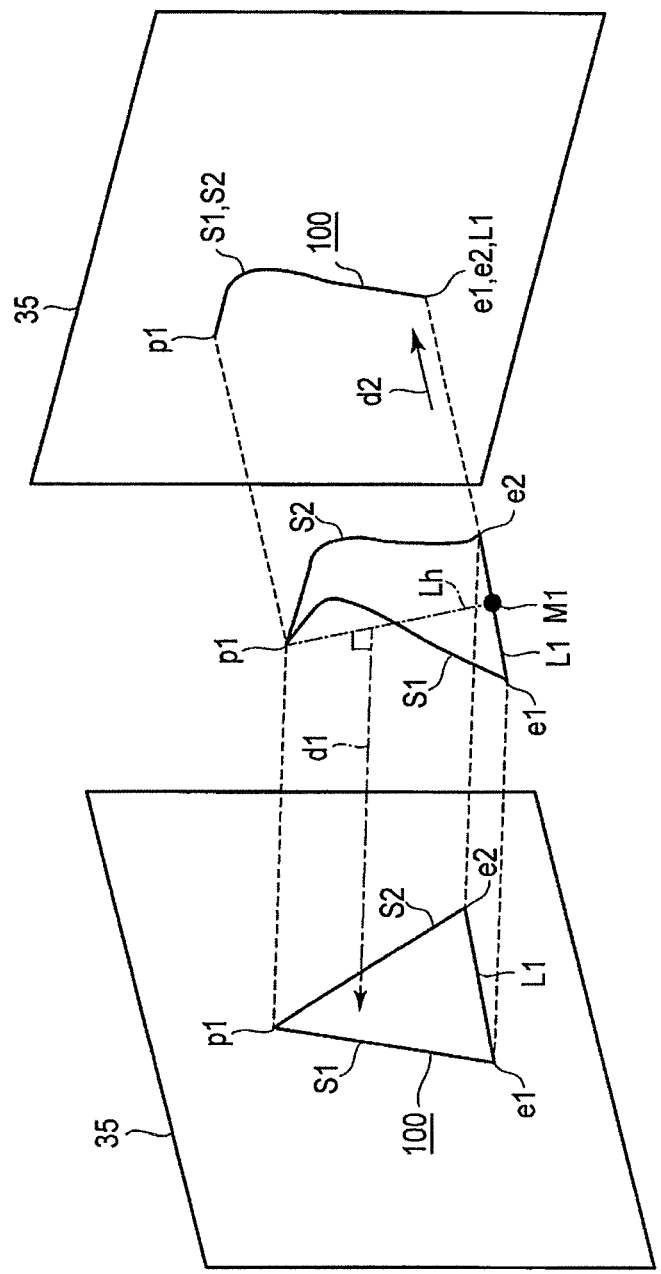
FIG. 20 is a schematic diagram illustrating the imaging direction in the sixth embodiment.

Even if the graphic enclosed by the safety lines S1, S2 and the valve boundary line L1 forms a curved surface as depicted in FIG. 20, the imaging directions d1, d2 can also be determined. When the imaging direction d1 is determined using the valve boundary line L1 and the bisector Lh, the imaging direction d1 may not necessarily correspond to the maximum projection area but can be easily and quickly determined. The imaging direction d2 may be a direction parallel to the valve boundary line L1, and the number of pixels enclosed by a generally L-shaped curve on the two-dimensional space in the right of FIG. 20 may be determined.

The remaining part of the configuration of the sixth embodiment is similar to the corresponding part in each of the first to fifth embodiments.

In the configuration as described above, the imaging direction defined by each of the arms 91, 191 is controlled by the projection area of the surface formed by the navigation graphic. Thus, in addition to producing the same effects as those of the first to fifth embodiments and each variation, the sixth embodiment can make the navigation graphic in the displayed superimposed image easy to see.

For example, when the inserted clip 102 is advanced, a relation between the valve boundary line L1 and the rotation angle of the clip 102 can be made more easily visible by setting the imaging direction d1 perpendicular to the valve boundary line L1. Thus, when a triangle is generated, the position of the Ω arm 191 is controlled to set the imaging direction d1 in which the triangle has the largest projection area. For the imaging direction d2 perpendicular to the imaging direction d1, setting the imaging direction d2 parallel to the valve boundary line L1 allows the triangle to be projected into a single line, facilitating viewing of a relation between the position of the valve boundary line L1 and a traveling direction of the clip 102. Thus, before and after rotation of the Ω arm 191, the position of the C arm 91 is controlled to set the imaging direction d2 in which the triangle has the minimum projection area.

<Modification>

A modification of the sixth embodiment is an aspect which does not use the X-ray diagnosis apparatus 1 and where, in order to make the navigation graphic 100 easy to see, the ultrasonic diagnosis apparatus 120 controls display of slices based on the projection area of the surface formed by the navigation graphic 100.

Basically, the graphic generation function 1372 has functions similar to those of the graphic generation function 372 described with reference to FIG. 19 and FIG. 20. However, the graphic generation function 1372 of the ultrasonic diagnosis apparatus 120 has functions different from the functions of the graphic generation function 372 in conjunction with the non-use of the arms 91, 191.

Figure 21:
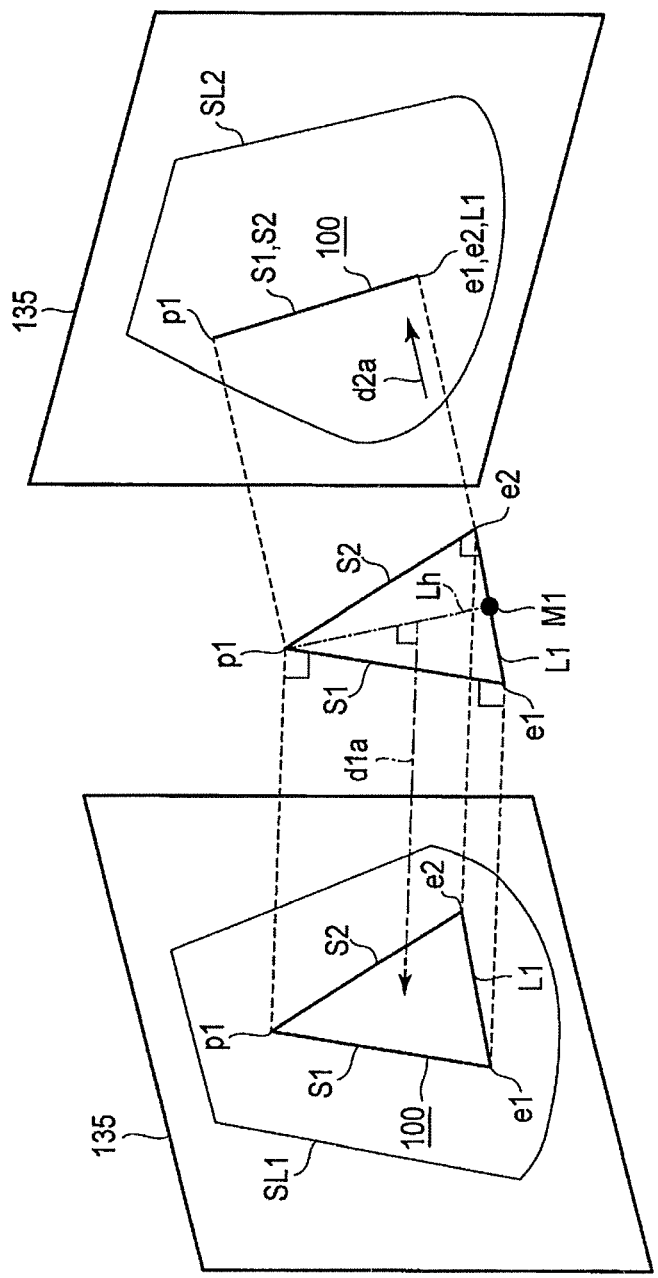
FIG. 21 is a schematic diagram illustrating a modification of the sixth embodiment.

That is, as depicted in FIG. 21, the graphic generation function 1372 generates a navigation graphic 100 including the safety lines S1, S2 and the valve boundary line L1. Subsequently, the graphic generation function 1372 delivers to the transmission/reception circuitry 123 a command for scan of a first slice SL1 orthogonal to a projection direction d1a in which the projection area of the surface formed by the navigation graphic 100 is maximized. Based on the command, the transmission/reception circuitry 123 controls the ultrasonic probe 121 based on TEE. The projection direction d1a corresponds to the above-described imaging direction d1. As described above, a triangle on the three-dimensional space in the center of FIG. 21 is parallel to a triangle on the two-dimensional space in the left of FIG. 21. The first slide SL1 as described above may be determined to be a plane in the two-dimensional space comprising the puncture point p1 and the ends e1, e2 of the valve boundary line L1. When the first slice SL1 is determined, the projection area need not be determined.

The graphic generation function 1372 delivers to the transmission/reception circuitry 123 a command for scan of a second slice SL2 which is orthogonal to a projection direction d2a perpendicularly crossing the current projection direction d1a. Based on the command, the transmission/reception circuitry 123 controls the ultrasonic probe 121. For the current second slice SL2, the surface formed by the navigation graphic 100 has the minimum projection area.

The second slice SL2 as described above may be determined to be, for example, a plane in the two-dimensional space which is orthogonal to the valve boundary line L1 and which comprises the middle point M1 of the valve boundary line L1 and the puncture point p1. The middle point M1 may be replaced with one of the back-flow positions r1, r2. When the second slice SL2 is determined, the projection area need not be determined.

As depicted in FIG. 22, even if the graphic enclosed by the safety lines S1, S2 and the valve boundary line L1 forms a curved surface, the first slice and the second slice SL2 can be determined.

The modification as described above allows the ultrasonic diagnosis apparatus 120 to also produce effects similar to those in the sixth embodiment.

Seventh Embodiment

A seventh embodiment is a modification of the first to sixth embodiments in which an image processing apparatus 230 is provided as an external apparatus for the X-ray diagnosis apparatus 1 and the ultrasonic diagnosis apparatus 120. The image processing apparatus 230 comprises at least one of a memory 231, an input interface 233, a display 235, processing circuitry 237, and a communication interface 239. The processing circuitry 237 comprises a processor and a memory not depicted in the drawings. The processor of the processing circuitry 237 invokes and executes a program in the memory 231 to implement a setting function 2371, a graphic generation function 2372, a superimposed image generation function 2373, or a display control function 2374 corresponding to the program.

The image processing apparatus 230 can communicate with each of the X-ray diagnosis apparatus 1 and the ultrasonic diagnosis apparatus 120 via the network, and has functions similar to those of the image processing apparatuses 30, 130 of the X-ray diagnosis apparatus 1 and the ultrasonic diagnosis apparatus 120, respectively. Each of the image processing apparatuses 30, 130, 230 is an example of an image processing apparatus recited in the claims. Thus, for description of the image processing apparatus 230, duplicate detailed descriptions are omitted from the descriptions of the image processing apparatus 30, 130 of the above-described diagnosis apparatuses 1, 120, with the digit in the hundreds place changed to 2.

That is, the memory 231 is configured similarly to the above-described memories 31, 131, and stores first medical images of the cardiac area of the object pre-acquired in a plurality of directions and a second medical image of the cardiac area acquired in real time. The second medical image is generated and transmitted by the X-ray diagnosis apparatus 1 or the ultrasonic diagnosis apparatus 120, and received by the communication interface 239 and then written to the memory 231. The first medical images and the second medical image are as described above. The memory 231 stores a program for the image processing apparatus 230.

The input interface 233 is configured similarly to the above-described input interface 33, 133, and outputs en electric signal corresponding to an operation by the operator to the processing circuitry 237.

The display 235 is configured similarly to the above-described displays 35, 135 and controlled by the processing circuitry 237 to display the medical images, the navigation graphic, and the superimposed image.

The processing circuitry 237 is configured similarly to the above-described processing circuitry 37, 137, and comprises a processor and a memory not depicted in the drawings. Various types of information input or set by the input interface 233 are saved to the memory. The processor of the processing circuitry 237 invokes and executes a program in the memory 231 to implement a setting function 2371, a graphic generation function 2372, a superimposed image generation function 2373, or a display control function 2374 corresponding to the program.

The setting function 2371 is a function similar to the above-described setting functions 371, 1371, and sets each of the valve boundary line indicating the boundaries between the leaflets of the heart valve in the cardiac chamber and the puncture point on the inner wall of the cardiac chamber through which the catheter is inserted.

The graphic generation function 2372 is a function similar to the above-described graphic generation functions 372, 1732, and generates a plurality of safety lines S1, S2 individually connecting the puncture point p1 to the ends e1, e2 of the valve boundary line at a distance from the inner wall to generate a navigation graphic 100 comprising the valve boundary line L1 and the safety lines S1, S2.

The superimposed image generation function 2373 is configured similarly to the above-described superimposed image generation functions 373, 1373, to superimpose the navigation graphic on the second medical image to generate a superimposed image.

The display control function 2374 is configured similarly to the above-described display control functions 374, 1374 to allow the display 235 to display the superimposed image.

The communication interface 239 is a circuit configured similarly to the above-described communication interfaces 39, 139 to communicate with an external apparatus by wire, by radio, or by both. The external apparatus is as described above, and in particular, comprises the X-ray diagnosis apparatus 1 or the ultrasonic diagnosis apparatus 120 as a modality.

The image processing apparatus 230 as described above functions as the image processing apparatus 30 in the X-ray diagnosis apparatus 1 provided as an external apparatus. Alternatively, the image processing apparatus 230 functions as the image processing apparatus 130 in the ultrasonic diagnosis apparatus 120 provided as an external apparatus.

In the configuration as described above, the image processing apparatus 230 provided as an external apparatus for the X-ray diagnosis apparatus 1 and the ultrasonic diagnosis apparatus 120 can operate similarly to the image processing apparatuses 30, 130 in each of the first to sixth embodiments and each modification to produce effects similar to those of each of the first to sixth embodiments and each modification.

In at least one of the above-described embodiments, each of the valve boundary line indicating the boundaries between the leaflets of the heart valve in the cardiac chamber and the puncture point on the inner wall of the cardiac chamber through which the catheter is inserted is set based on the first medical image. A plurality of safety lines are generated which individually connect the puncture point to the ends of the valve boundary line at a distance from the inner wall, and thus, a navigation graphic comprising the valve boundary line and the safety lines is generated. The navigation graphic is superimposed on the second medical image to generate a superimposed image. The superimposed image is displayed on the display. Therefore, the embodiments allow provision of a navigation graphic which enables improvement of safety and accuracy of the catheter treatment.

The term "processor" used in the above description means, for example, a CPU (Central Processing Unit), a GPU (Graphics Processing Unit), or circuitry such as an ASIC (Application Specific Integrated Circuit), or a programmable logic device (e.g. SPLD (Simple Programmable Logic Device), CLPD (Complex Programmable Logic Device), FPGA (Field Programmable Gate Array)). The processor realizes functions by reading out and executing programs stored in the memory circuitry. In the meantime, instead of storing programs in the memory circuitry, such a configuration may be adopted that programs are directly incorporated in the circuitry in the processor. In this case, the processor realizes functions by reading out and executing programs stored in the circuitry. Each of the processors in the embodiments may not be configured as single circuitry for each processor. A plurality of independent circuitries may be constructed as a single processor, and the functions of the processor may be realized. Furthermore, a plurality of structural elements in FIG. 2, FIG. 15 and FIG. 23 may be integrated in a single processor, and the functions of the processor may be realized.

In FIG. 2, a case of using the memory 31 as a single memory is illustrated; however, the above-described embodiments are not limited to this case. The embodiments may be modified to use a plurality of memories that are independently arranged, instead of a single memory 31. In a case of this modification, it is possible to cause different memories to separately store the first medical image and the second medical image. Such a modification is similarly implementable for the memory 131 in FIG. 15 and the memory 231 in FIG. 23.

Figure 24:
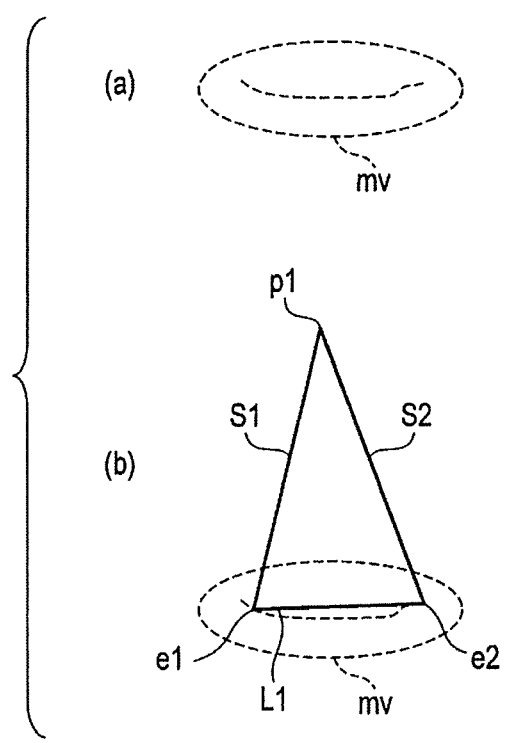
FIG. 24 is a schematic diagram illustrating safety lines in each of the embodiments.

In the above description, as depicted in FIG. 24(a) and FIG. 24(b), the puncture point p1 and the ends e1, e2 of the valve boundary line L1 are set for the mitral valve my with the two leaflets (cusps) to generate a plurality of safety lines S1, S2, by way of example. However, the number of leaflets may be three. The embodiments are not limited to the case where the catheter is stuck into the cardiac wall and inserted into the left atrium LA or the like. The catheter may be inserted into the right atrium RA through the vein without being stuck into the cardiac wall.

Figure 25:
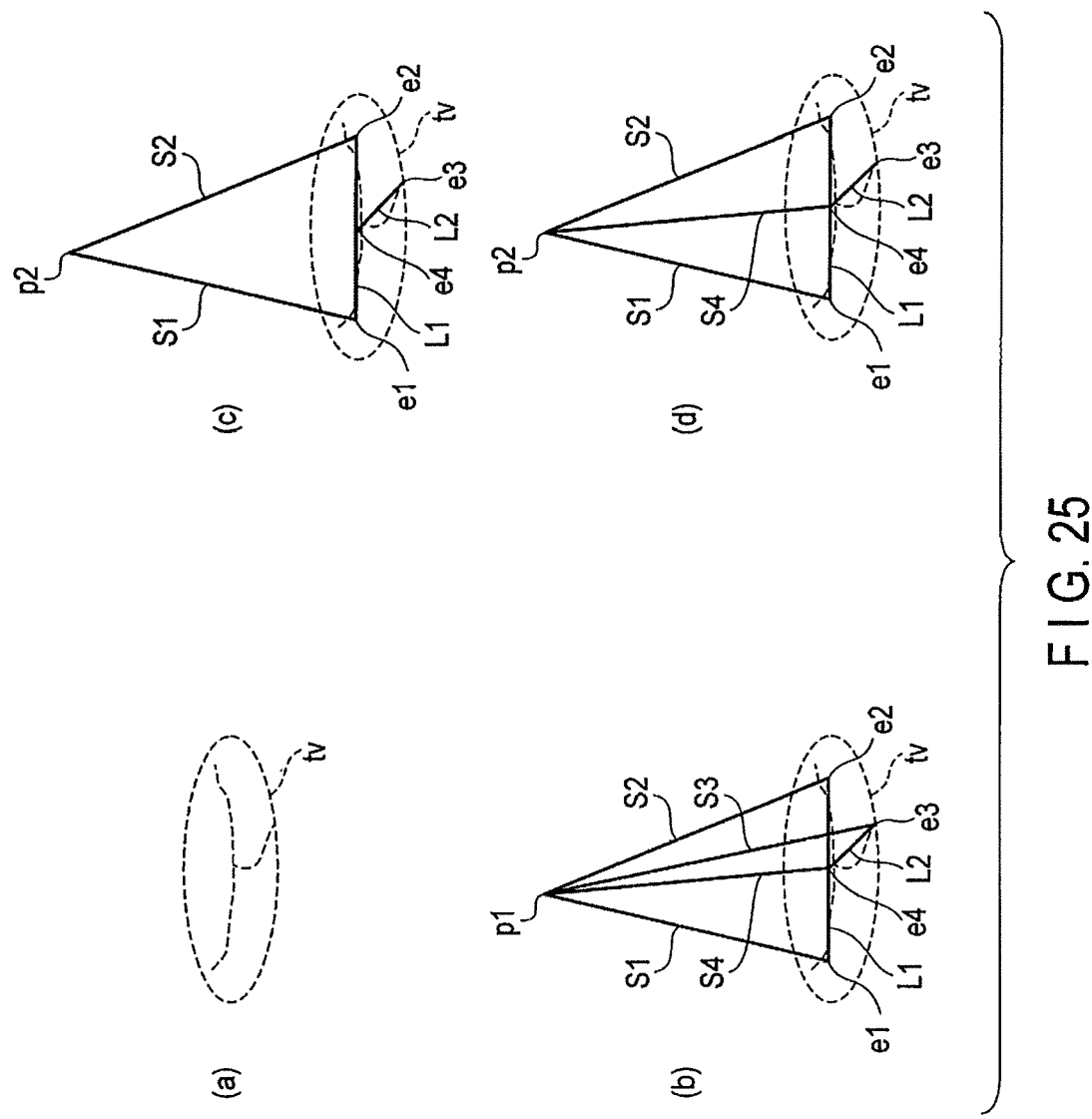
FIG. 25 is a schematic diagram illustrating safety lines in a modification of each of the embodiments.

That is, in each of the above-described embodiments and each modification, an insertion point p2 and ends e1 to e4 of valve boundary lines L1 and L2 may be set for a tricuspid valve tv with three leaflets (cusps) to generate a plurality of safety lines S1 to S4, as depicted in FIG. 25(a) and FIG. 25(b). The configuration for the tricuspid valve tv is not limited to the example illustrated in FIG. 25(b), the number of safety lines S1, . . . may be reduced as needed. For example, as depicted in FIG. 25(c), the two inner safety lines S3, S4 may be omitted, and the outer safety lines S1, S2 may be generated. In this case, the valve boundary lines L1 and L2 can be made easily visible. Likewise, as depicted in FIG. 25(d), the safety lines S3, located closer to the reader, may be omitted, and the outer and central safety lines S1, S2, S4 may be generated. This also allows the valve boundary lines L1 and L2 to be made easily visible. Alternatively, besides the modifications illustrated in FIG. 25(c) and FIG. 25(d), other safety lines may be omitted as desired.

Figure 26:
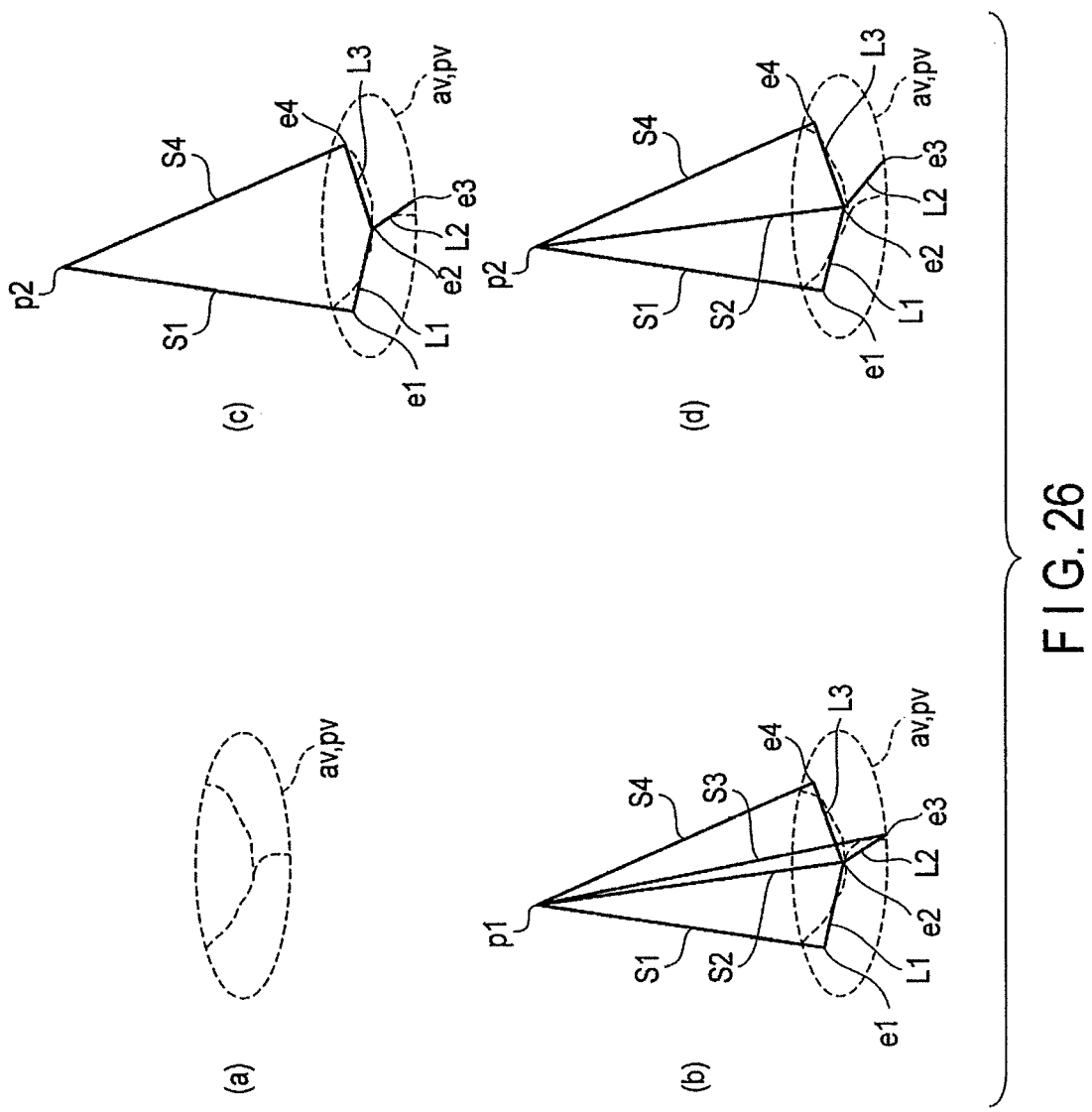
FIG. 26 is a schematic diagram illustrating safety lines in another modification of each of the embodiments.

For the aortic valve av or the pulmonary valve pv with three leaflets (cusps), a plurality of safety lines S1 to S4 can be generated by setting an insertion point p2 for puncture or insertion and ends e1 to e4 of valve boundary lines L1 to L3 as depicted in FIG. 26(a) and FIG. 26(b). In this case, for example, as depicted in FIG. 26(c) and FIG. 26(d), the valve boundary lines L1 to L3 can similarly be made easily visible by reducing the number of safety lines S1, . . . As needed. Alternatively, besides the modifications illustrated in FIG. 26(c) and FIG. 25(d), other safety lines may be omitted as desired. The settings illustrated in FIG. 26 may be applied to the tricuspid valve tv.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An image processing apparatus comprising:
at least one of memory configured to store a first medical image of a heart area of a subject acquired in a plurality of directions and a second medical image of the heart area acquired in real time; and
processing circuitry configured to
set, based on the first medical image, a valve boundary line indicating a boundary between leaflets of a heart valve in a heart chamber and an insertion point on an inner wall of the heart chamber through which a catheter is inserted, wherein the insertion point is set on the first medical image based on an operation received by an input interface, and wherein the insertion point is set after the inner wall is punctured for insertion of the catheter and represents a puncture point,
generate a navigation graphic including the valve boundary line and safety lines by generating a plurality of safety lines individually connecting the insertion point to ends of the valve boundary line at a distance from the inner wall,
superimpose the navigation graphic on the second medical image to generate a superimposed image, and
display the superimposed image on a display.

2. The image processing apparatus according to claim 1, wherein the processing circuitry is configured to update the navigation graphic by updating the plurality of safety lines such that the plurality of safety lines individually connect a tip of the catheter or a position where the catheter is inserted, which replaces the insertion point, to the ends of the valve boundary line after, on the superimposed image, the catheter is inserted through the inner wall.

3. The image processing apparatus according to claim 2, wherein the navigation graphic forms a curved surface enclosed by the plurality of safety lines and the valve boundary line.

4. The image processing apparatus according to claim 3, wherein the navigation graphic is a graphic comprising, as corners, three points connecting two of the plurality of safety lines and the valve boundary line together.

5. The image processing apparatus according to claim 2, wherein the plurality of safety lines substantially overlap one another to indicate a trajectory of the catheter when the second medical image is acquired in a first direction in which a projected area of a surface formed by the navigation graphic is minimized.

6. The image processing apparatus according to claim 2, wherein each of the plurality of safety lines indicates a limit of a trajectory of the catheter when the second medical image is acquired in a second direction in which a projected area of a surface formed by the navigation graphic is maximized.

7. The image processing apparatus according to claim 2, wherein the processing circuitry is configured to set at least one back-flow position in the heart valve, on the valve boundary line, update the valve boundary line such that the valve boundary line includes a graphic indicating the back-flow position, and generate the navigation graphic such that the navigation graphic includes the updated valve boundary line and the plurality of safety lines.

8. The image processing apparatus according to claim 2, wherein the processing circuitry is configured to set at least one back-flow position in the heart valve, on the valve boundary line, connect the back-flow position to the insertion point to further generate at least one trajectory of the tip of the catheter, and generate the navigation graphic such that the navigation graphic further includes the trajectory.

9. The image processing apparatus according to claim 8, wherein
the heart chamber is a left atrium,
the heart valve is a mitral valve,
the inner wall is an atrial septum,
the tip of the catheter detachably holds a clip used to clip on the leaflets at the back-flow position, and
the processing circuitry is configured to execute, when a plurality of back-flow positions are set, an update process of updating the trajectory such that the trajectory connects the tip to one of the plurality of back-flow positions in accordance with advancement of the tip of the catheter passing through the insertion point, and repeatedly execute the update process until the clip is deployed at all the back-flow positions.

10. The image processing apparatus according to claim 2, wherein the first medical image is an X-ray volume image or a plurality of two-dimensional X-ray contrast images, and the second medical image is an X-ray fluoroscopic image.

11. The image processing apparatus according to claim 2, wherein the first medical image is an ultrasonic volume image, and the second medical image is an X-ray fluoroscopic image.

12. The image processing apparatus according to claim 2, wherein the first medical image is an ultrasonic volume image, and the second medical image is an ultrasonic image.

13. An X-ray diagnostic apparatus comprising:
an X-ray emitter configured to emit X-rays to a subject;
an X-ray detector configured to detect the X-rays;
an image generator configured to generate an X-ray image of a heart area of the subject in real time based on an output from the X-ray detector;
at least one of memory configured to pre-store a first medical image of the heart area acquired in a plurality of directions and to pre-store the generated X-ray image as a second medical image; and
processing circuitry configured to
set, based on the first medical image, a valve boundary line indicating a boundary between leaflets of a heart valve in a heart chamber and an insertion point on an inner wall of the heart chamber through which a catheter is inserted, wherein the insertion point is set on the first medical image based on an operation received by an input interface, and wherein the insertion point is set after the inner wall is punctured for insertion of the catheter and represents a puncture point,
generate a navigation graphic including the valve boundary line and safety lines by generating a plurality of safety lines individually connecting the insertion point to ends of the valve boundary line at a distance from the inner wall,
superimpose the navigation graphic on the second medical image to generate a superimposed image, and
display the superimposed image on a display.

14. The X-ray diagnostic apparatus according to claim 13, wherein the processing circuitry is configured to update the navigation graphic by updating the plurality of safety lines such that the plurality of safety lines individually connect a tip of the catheter which replaces the insertion point to the ends of the valve boundary line after, on the superimposed image, the catheter is inserted through the inner wall.

15. The X-ray diagnostic apparatus according to claim 14, wherein the navigation graphic forms a curved surface enclosed by the plurality of safety lines and the valve boundary line.

16. The X-ray diagnostic apparatus according to claim 14, wherein the navigation graphic is a graphic comprising, as corners, three points connecting two of the plurality of safety lines and the valve boundary line together.

17. An ultrasonic diagnostic apparatus comprising:
an ultrasonic probe configured to transmit an ultrasonic wave to a subject and to receive a reflected wave of the ultrasonic wave;
an image generator configured to generate an ultrasonic image of a heart area of the subject in real time based on an output from the ultrasonic probe;
at least one of memory configured to pre-store a first medical image of the heart area acquired in a plurality of directions and to pre-store the generated ultrasonic image as a second medical image; and
processing circuitry configured to
set, based on the first medical image, a valve boundary line indicating a boundary between leaflets of a heart valve in a heart chamber and an insertion point on an inner wall of the heart chamber through which a catheter is inserted, wherein the insertion point is set on the first medical image based on an operation received by an input interface, and wherein the insertion point is set after the inner wall is punctured for insertion of the catheter and represents a puncture point,
generate a navigation graphic including the valve boundary line and safety lines by generating a plurality of safety lines individually connecting the insertion point to ends of the valve boundary line at a distance from the inner wall,
superimpose the navigation graphic on the second medical image to generate a superimposed image, and
display the superimposed image on a display.

18. An image processing apparatus comprising:
at least one of memory configured to store a first medical image of a heart area of a subject acquired in a plurality of directions and a second medical image of the heart area acquired in real time; and
processing circuitry configured to
set, based on the first medical image, each of a valve boundary line indicating a boundary between leaflets of a heart valve in a heart chamber and an insertion point on an inner wall of the heart chamber through which a catheter is inserted,
generate a navigation graphic including the valve boundary line and safety lines by generating a plurality of safety lines individually connecting the insertion point to ends of the valve boundary line at a distance from the inner wall, superimpose the navigation graphic on the second medical image to generate a superimposed image, and display the superimposed image on a display, wherein the processing circuitry is configured to update the navigation graphic by updating the plurality of safety lines such that the plurality of safety lines individually connect a tip of the catheter or a position where the catheter is inserted, which replaces the insertion point, to the ends of the valve boundary line after, on the superimposed image, the catheter is inserted through the inner wall, set at least one back-flow position in the heart valve, on the valve boundary line, connect the back-flow position to the insertion point to further generate at least one trajectory of the tip of the catheter, and generate the navigation graphic such that the navigation graphic further includes the trajectory.

19. The image processing apparatus according to claim 18, wherein the heart chamber is a left atrium, the heart valve is a mitral valve, the inner wall is an atrial septum, the tip of the catheter detachably holds a clip used to clip on the leaflets at the back-flow position, and the processing circuitry is configured to execute, when a plurality of back-flow positions are set, an update process of updating the trajectory such that the trajectory connects the tip to one of the plurality of back-flow positions in accordance with advancement of the tip of the catheter passing through the insertion point, and repeatedly execute the update process until the clip is deployed at all the back-flow positions.

* * * * *